(12) United States Patent
Morris

(10) Patent No.: US 8,246,550 B2
(45) Date of Patent: Aug. 21, 2012

(54) COMPREHENSIVE INTEGRATED TESTING PROTOCOL FOR INFANT LUNG FUNCTION

(75) Inventor: Mohy G. Morris, Little Rock, AR (US)

(73) Assignees: Board of Trustees of the University of Arkansas, Little Rock, AR (US); Arkansas Children's Hospital Research Institute, Inc., Little Rock, AR (US)

(*) Notice: Subject to any disclaimer, the term of this patent is extended or adjusted under 35 U.S.C. 154(b) by 1314 days.

(21) Appl. No.: 11/985,416

(22) Filed: Nov. 15, 2007

(65) Prior Publication Data

US 2009/0131811 A1    May 21, 2009

(51) Int. Cl.
*A61B 5/08* (2006.01)
(52) U.S. Cl. .................................. 600/538; 600/529
(58) Field of Classification Search .............. 600/538, 600/539, 540, 541, 542, 529
See application file for complete search history.

(56) References Cited

U.S. PATENT DOCUMENTS

| | | | |
|---|---|---|---|
| RE28,513 | E | 8/1975 | Suzuki et al. |
| 4,307,730 | A | 12/1981 | Korn |
| 4,333,476 | A | 6/1982 | Downing et al. |
| 4,796,639 | A | 1/1989 | Snow et al. |
| 5,119,825 | A | 6/1992 | Huhn |
| 5,513,647 | A * | 5/1996 | Castile .................. 600/538 |
| 5,540,233 | A | 7/1996 | Larsson et al. |
| 5,957,128 | A | 9/1999 | Hecker et al. |
| 6,139,506 | A | 10/2000 | Heinonen |
| 6,306,099 | B1 * | 10/2001 | Morris .................... 600/529 |
| 7,108,666 | B2 * | 9/2006 | Stenzler .................. 601/44 |

OTHER PUBLICATIONS

Morris, M., The Open Circuit Nitrogen Washout Technique for Measuring the Lung Volume in Infants, Thorax 54: 790-795, 1999.*

Castile, R., et al., Adult-Type Pulmonary Function Tests in Infants without Respiratory Disease, Pediatric Pulmonology 30: 215-227, 2000.

Eccles, R., The Nasal Cycle in Respiratory Defence, Acta oto-rhino-laryngologica belg. 54:281-286, 2000.

Eldridge, F., Posthyperventilation Breathing: Different Effects of Active and Passive Hyperventilation, Journal of Applied Physiology 34: 422-430, Apr. 1973.

(Continued)

*Primary Examiner* — Michael Kahelin
*Assistant Examiner* — Christian Jang
(74) *Attorney, Agent, or Firm* — Ray F. Cox, Jr.

(57) ABSTRACT

A Comprehensive Integrated Testing Protocol (CITP) incorporates precise measurements of the dynamic and the static lung volumes and capacities at $V_{30}$ for routine infant lung function testing. The static functional residual capacity (sFRC) in infants is measured after a short hyperventilation induces a post-hyperventilation apnea (PHA) that abolishes the infant's breathing strategies and creates a reliable volume landmark. A measurement of the sFRC is then obtained by inert gas washout; e.g., by measuring the volume of nitrogen expired after end-passive expiratory switching of the inspired gas from room air to 100% oxygen during the PHA. A true measurement of the total lung capacity (TLC) is obtained from the sum of (1) the passively exhaled gas volume from a Pao plateau of 30 cm $H_2O$ through a pneumotachometer (PNT) by integrating the flow signal to produce volume, which is the inspiratory capacity (IC), and (2) the sFRC. From intrasubject TLC and residual volume (RV), the difference is a reliable estimate of the slow vital capacity (SVC). Similar measurements may be obtained with a fastened squeeze jacket for comparison. Actual airway opening pressure (aPao) is measured during a 0.20 s airway occlusion after halting the inflating airflow and prior to activating the jacket inflation. An open mouth is maintained during forced expiration in order to generate an oronasal instead of a forced expiration.

25 Claims, 12 Drawing Sheets

SUBDIVISIONS OF INFANT LUNG VOLUME ($V_{30}$) AT AN AIRWAY OPENING PRESSURE OF 30 CM $H_2O$

OTHER PUBLICATIONS

Feher, A., et al., Flow Limitation in Normal Infants: A New Method for Forced Expiratory Maneuvers from Raised Lung Volumes, J. Appl. Physiol 80:2019-2025, 1996.

Hall, G., et al., Contribution of Nasal Pathways to Low Frequency Respiratory Impedance in Infants, Thorax 57: 396-399, 2002.

Hammer, J., et al., Total Lung Capacities by N2 Washout from High and Low Lung Volumes in Ventilated Infants and Children, Am J Respir Crit Care Med 158:526-531, 1998.

Hayden, M., et al., Influence of Driving Pressure on Raised-volume Forced Expiration in Infants, Am J Respir Crit Care Med 156:1876-1883, 1997.

Hayden, M., et al., Methacholine Responsiveness Using the Raised Volume Forced Expiration Technique in Infants, Am J Respir Crit Care Med 155: 1670-1675, 1997.

Hayden, M., et al., Bronchodilator Responsiveness Testing Using Raised Volume Forced Expiration in Recurrently Wheezing Infants, Pediatric Pulmonology 26: 35-41, 1998.

Jones, M., et al., Flow Limitation in Infants Assessed by Negative Expiratory Pressure, Am J Respir Crit Care Med 161: 713-717, 2000.

Jones, M., et al., Sensitivity of Spirometric Measurements to Detect Airway Obstructin in Infants, Am J Respir Crit Care Med 167: 1283-1286, 2003.

Jones, M., et al., Forced Expiratory Flows and Volumes in Infants, Am J Respir Crit Care Med 161: 353-359, 2000.

Ljungberg, H., et al., Infant Lung Function Testing: Available and Useful Methods, Breathe 1: 13-23, Sep. 2004.

Lum, S., et al., Effect of Raised Lung Volume Technique on Subsequent Measures of VmaxFRC in Infants, Pediatric Pulmonology 38: 146-154, 2004.

Lum, S., et al., Influence of Jacket Tightness and Pressure on Raised Lung Volume Forced Expiratory Maneuvers in Infants, Pediatric Pulmonology 34: 361-368, 2002.

Lum, S., et al., Effect of Airway Inflation Pressures on Forced Expiratory Maneuvers from Raised Lung Volume in Infants, Pediatric Pulmonology 33: 130-134, 2002.

Lum, S., et al., Lung Function Tests in Neonates and Infants with Chronic Lung Disease: Forced Expiratory Maneuvers, Pediatric Pulmonology 41: 199-214, Nov. 15, 2005.

McCoy, K., et al., Functional Residual Capacity (FRC) Measurements by Plethysmography and Helium Dilution in Normal Infants, Pediatric Pulmonology, 19: 282-290, 1995.

Modl, M., et al., Assessments of Bronchodilator Responsiveness in Infants with Bronchiolitis, Am J Respir Crit Care Med 161: 763-768, 2000.

Modl, M., et al., Reproducibility of Forced Expiratory Flow and Volume Measurements in Infants with Bronchiolitis, Pediatric Pulmonology 28: 429-435, 1999.

Morris, M., Abstract, A New Technique to Measure Residual Volume (RV), 1999 ALA/ATS International Conference, San Diego CA, Apr. 27, 1999, 1 page.

Morris, M., A Simple New Technique to Measure the Effective Dead Space of the Face Mask with a Water Volumeter in Infants, Eur Respir J 14: 1163-1166, 1999.

Morris, M., The Bias Flow Nitrogen Washout Technique for Measuring the Functional Residual Capacity in Infants, Eur Respir J 17: 529-536, 2001.

Morris, M., A Novel Non-invasive Technique for Measuring the Residual Lung Volume by Nitrogen Washout with Rapid Thoracoabdominal Compression, Thorax 54: 874-883, 1999.

Ofodile, F., et al., The Black American Nose, Ann Plast Surg 31: 209-219, Sep. 1993.

Pertuze, J., et al., Maximum Airflow Through the Nose in Humans, J. Appl. Physiol. 70: 1369-1376, 1991.

Pickering, D., et al., Nasal Flow Limitation in Children, Pediatric Pulmonology 27: 32-36, 1999.

Ranganathan, S., et al., Exploring the Relationship Between Forced Maximal Flow at Functional Residual Capacity and Parameters of Forced Expiration from Raised Lung Volumes in healthy infants, Pediatric Pulmonology 33: 419-428, 2002.

Ranganathan, S., et al., Relative Ability of Full and Partial Forced Expiratory Maneuvers to Identify Diminished Airway Function, Am J Respir Crit Care Med 166: 1350-7, 2002.

Ranganathan, S., Airway Function in Infants Newly Diagnosed with Cystic Fibrosis, The Lancet 358: 1964-65, Dec. 8, 2001.

Sededin, E., et al., Nasal Airway Versus Oral Route for Infant Resucitation, The Lancet 346: 382, Aug. 5, 1995.

Stocks, J., et al., Nasal Resistance During Infancy, Respiration Physiology 34: 233-246, 1978.

Turner, D., et al., A New Technique to Generate and Assess Forced Expiration from Raised Lung Volume in Infants, Am J Respir Crit Care Med 151: 1441-1450, 1995.

Wilson-Davis, S., et al., Air Entry in Infant Resuscitation: Oral or Nasal, J. App. Physiol. 82: 152-155, 1997.

ATS/ERS Statement: Raised Volume Forced Expirations in Infants, Am J Respir Crit Care Med 172: 1463-1471, 2005.

ATS/ERS Consensus Statement (On-line Supplement), Raised Volume Forced Expirations in Infants, pp. 1-21, Mar. 3, 2004.

Stocks, J., Lung Function Testing in Infants, Pediatric Pulmonology, Supplement 18, 14-20, 1999.

* cited by examiner

SUBDIVISIONS OF INFANT LUNG VOLUME ($V_{30}$) AT AN AIRWAY OPENING PRESSURE OF 30 CM $H_2O$

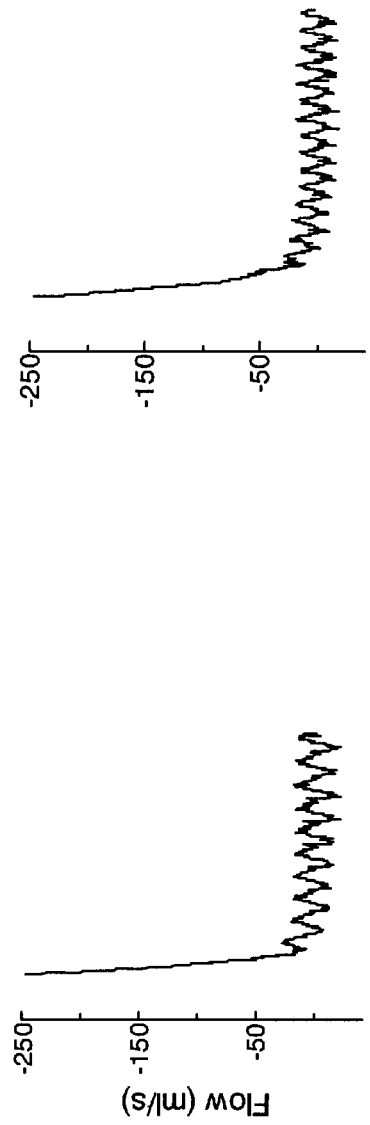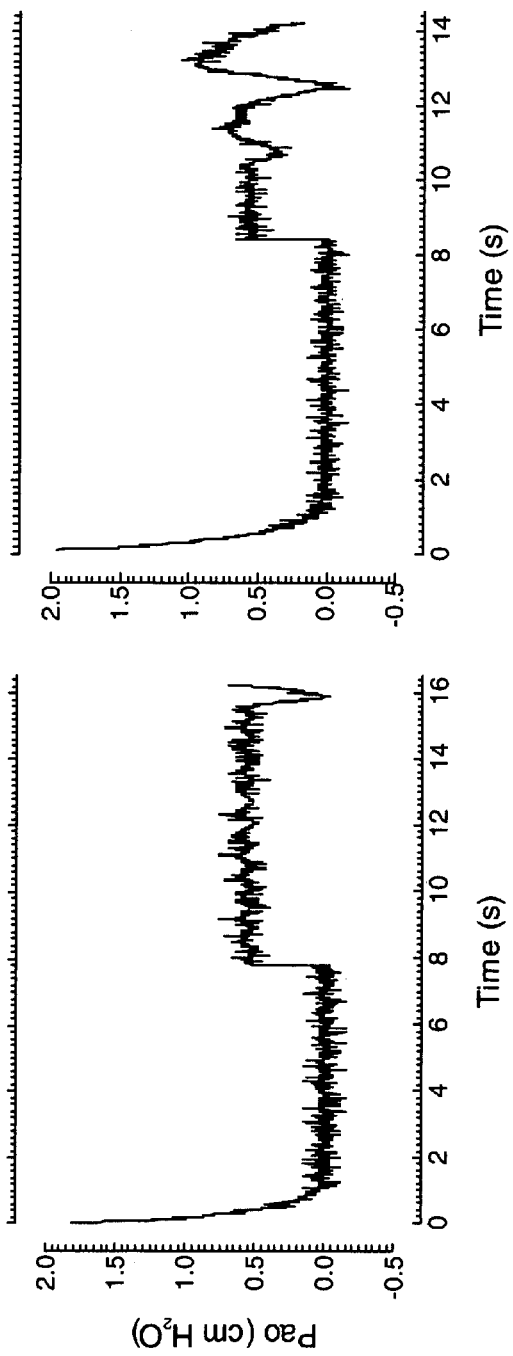

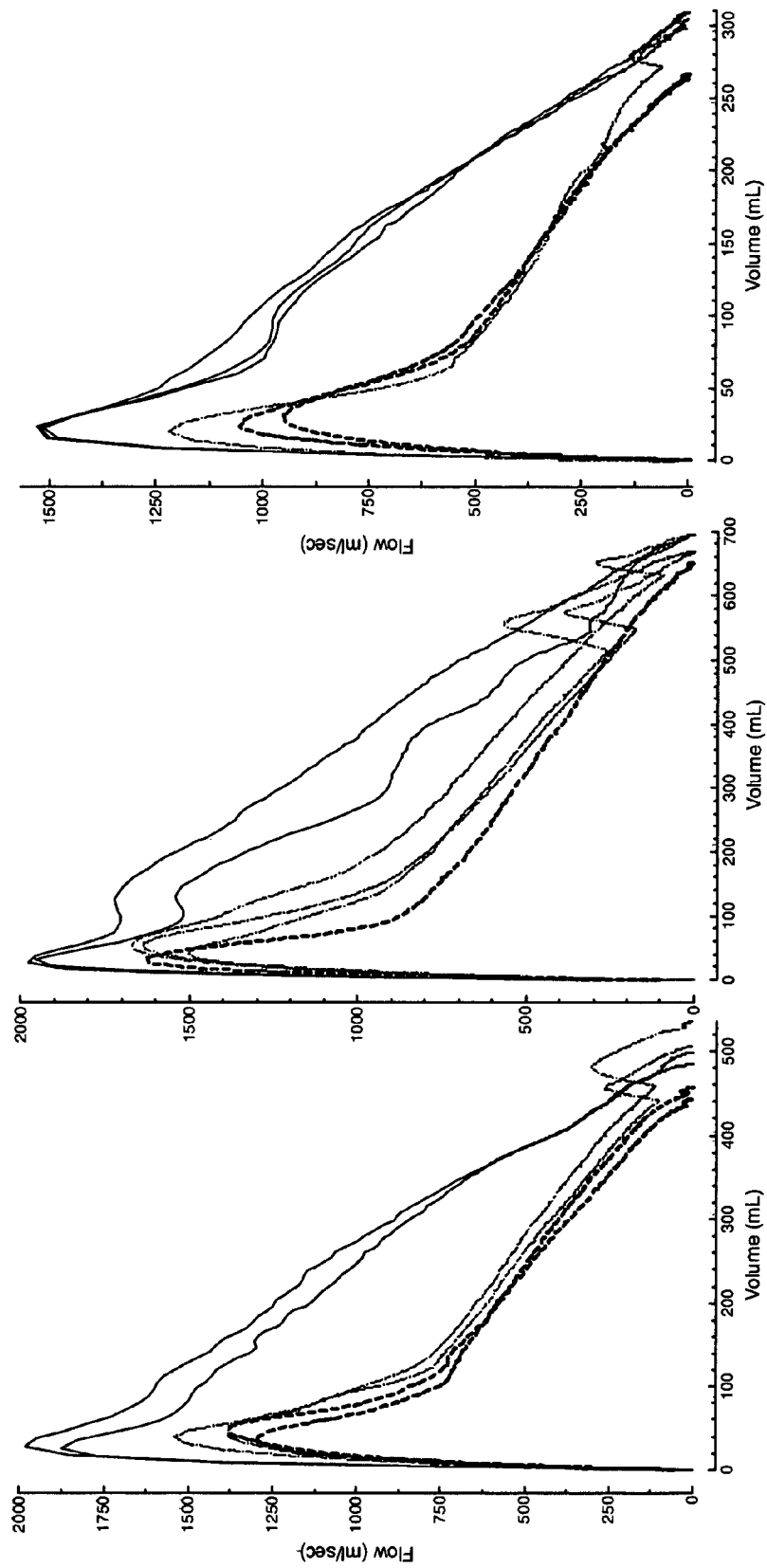

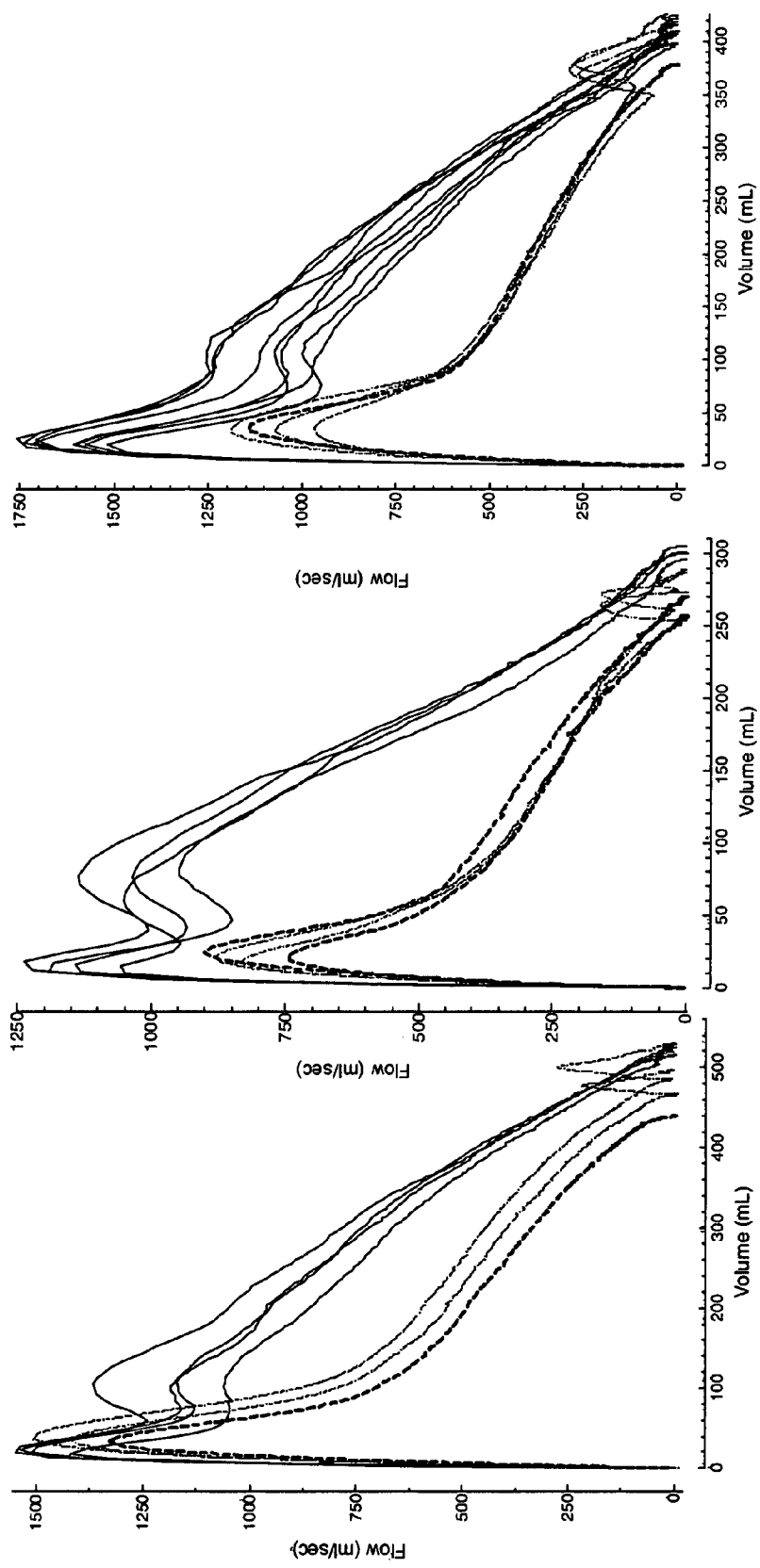

COMPREHENSIVE INTEGRATED TESTING PROTOCOL FOR INFANT LUNG FUNCTION

STATEMENT REGARDING FEDERALLY SPONSORED RESEARCH OR DEVELOPMENT

This invention was made with Government support under the terms of Grant No. 1 K23 HL04475-01A1 awarded by NHLBI. The Government has certain rights in the invention.

CROSS-REFERENCE TO RELATED APPLICATIONS

Not applicable.

BACKGROUND OF THE INVENTION

1. Field of the Invention

The present invention relates to a testing protocol for infant lung function.

2. Brief Description of the Related Art

Lung function testing (LFT) is an established mostly standardized routine diagnostic modality in clinical medicine for older cooperative children and adults but not infants. Since infants cannot cooperate, infant lung function testing (ILFT) is more tedious and lengthy to accomplish. It is operator, technique(s), hardware and software-dependent and is performed with the infant lying supine using a facemask during a limited unpredictable period of a chloral hydrate-induced sleep. The drug use precludes repeat or frequent testing.

Therefore, ILFT has for many years often been confined to relatively insensitive tests within the normal tidal breathing range.

Despite being an unreliable volume landmark in infants and young children, the functional residual capacity (FRC), which is the residual gas in the lungs and airways and represents the oxygen stores at end-tidal expiration, has until recently been the only lung volume to be routinely and reliably measured in this inherently uncooperative age-group. FRC measurement is primarily important for defining the normal lung growth and development, in assessing longitudinally a suspected impairment of alveolar growth and for interpreting lung mechanics and tidal expiratory flows.

With normal tidal breathing in adults and older children the normal end-expiratory lung volume, that is the static or passive FRC coincides with the elastic equilibrium volume (EEV) of the respiratory system where the outward recoil of the chest wall is balanced by the inward recoil of the lungs. In infancy, the compliance of the chest wall is nearly threefold that of the lung. By the second year of life, the increase in chest wall stiffness is such that the child's chest wall and lung have similar compliances, as in adults. Hence, in infants, the outward recoil of the chest wall is very small and the inward recoil of the lung slightly less than in adults. Therefore, the balance of the elastic recoil forces of the lung and chest wall in the infant predicts a very low FRC of only 10% of the total lung capacity (TLC), which is incompatible with the appropriate stability of the peripheral airways or adequate gas exchange. Therefore, infants incorporate breathing strategies which include postinspiratory activity of the diaphragm, laryngeal narrowing during inspiration and braking of expiration to maintain a dynamic FRC (dFRC) above the passively determined level, that is the static (sFRC) or passive FRC, and inspire before expiration ends passively. Compared to adults, infants terminate expiration at substantial flow rates. This breathing pattern results in a substantial increase in an end-expiratory lung volume above the passive level and a dynamic FRC/TLC ratio of 40% comparable to that of a supine adult. Taken together, any routine measurement of FRC in spontaneously breathing infants has always been a measurement of the dynamic FRC (dFRC) and the variability in end-expiratory level has impeded the assessment and interpretation not only of lung volumes but also of respiratory mechanics and forced expiratory flows.

Forced expiration (FE) is now widely generated with the rapid thoracoabdominal compression (RTC) technique using a squeeze jacket from a raised lung volume (RVRTC) mostly to an airway opening pressure (Pao) of 30 cm $H_2O$ which generates forced expiratory flow-volume (FEFV) curves in which flow limitation is better achieved. Nevertheless, the RVRTC technique remains fairly complex and difficult to perform and has neither been standardized nor its clinical utility established. Subtle changes and differences in methodology between various laboratories could lead to significant variations in the shape and smoothness of the FEFV curves generated and the instant or forced expiratory flows ($FEF_{\%}$) have been less reproducible than the volume-time ($FEV_t$) variables. With the rapid somatic growth and development in infants and changes in clinical status in those with disease, an impeccably high degree of repeatability and accuracy of simultaneous measurements of lung volume and airway function is essential in order to detect and quantify the earliest pathophysiological changes. It is especially significant that repeatability data on the same infant is lacking. The squeeze jacket placement and the need to repeat the RVRTC using increasing jacket pressures (Pj) until flow limitation is achieved may alter lung mechanics or influence subsequent measurements and other variables.

BRIEF SUMMARY OF THE INVENTION

In order to overcome the limitations of the prior art, the present invention is a Comprehensive Integrated Testing Protocol (CITP) which incorporates precise measurements of the dynamic and the static lung volumes and capacities at $V_{30}$ for routine ILFT. The CITP enables the analysis and investigation of the relation between measurements, such as a dynamic and a static volume or two static volumes, not only intra-subject but also within a single maneuver.

The present invention incorporates a method for measuring the static FRC (sFRC) in infants. The basic underlying concept is that passive hyperventilation has long been known to induce apnea in animals and humans. This post-hyperventilation apnea (PHA) has been used to generate forced expiration from a raised lung volume and for measuring the residual lung volume in infants. The present invention uses the technique of a short hyperventilation to induce a PHA that abolishes the infant's breathing strategies and creates a reliable volume landmark that is determined solely by the elastic equilibrium volume (EEV) of the infant's respiratory system. Therefore, a highly repeatable robust measurement of the static (sFRC) or passive FRC may then be obtained by measuring the remaining volume by any of various known inert gas washout techniques; e.g., by measuring the volume of nitrogen expired after end-passive expiratory switching of the inspired gas from room air to 100% oxygen during the PHA.

With the squeeze jacket unfastened during a PHA, a true measurement of the total lung capacity (TLC) is obtained from the sum of (1) the inspiratory capacity (IC) (measured for the first time), which is the passively exhaled gas volume from a Pao plateau of 30 cm $H_2O$ through a pneumotachometer (PNT) by integrating the flow signal to produce volume, which is the volume above the elastic equilibrium volume (EEV) of the infant's respiratory system, and (2) the residual gas volume, which is the static or passive (sFRC) functional residual capacity (FRC) (sFRC measured for the first time), measured as described above by an inert gas washout, such as the nitrogen washout technique after end-expiratory switching of the inspired gas from room air to 100% oxygen before the resumption of spontaneous inspiration.

U.S. Pat. No. 6,306,099, the disclosure of which is incorporated herein by reference, discloses measurement of the residual volume (RV) by nitrogen washout and the total lung capacity (fTLC) (the prefix "f" indicating a forced measurement) as the sum of (1) the forced vital capacity (FVC) from $V_{30}$ and (2) the RV. By measuring intrasubject TLC and RV, the difference between the two measurements is a reliable estimate of the slow vital capacity (SVC) which is useful to compare with the FVC when investigating air trapping.

Since the fastened jacket (j) could potentially limit chest wall expansion, another estimate of the slow vital capacity (jSVC) (the prefix "j" is used to indicate that the measurement is obtained with the squeeze jacket fastened around the chest and abdomen of the infant) is obtained by initiating RTC during the passive expiration from $V_{30}$ when the RV is measured with jTLC being the sum of these two variables. Measuring the jSVC, which could be equal to but might be smaller than SVC, provides an objective assessment of the extent of the known potential of the squeeze jacket to limit the infant's chest wall expansion during the lung inflation. The jTLC may also be compared with TLC and fTLC. The expiratory reserve volume (ERV) (previously described in Morris, M. G., A novel non-invasive technique for measuring the residual lung volume by nitrogen washout with rapid thoracoabdominal compression in infants, Thorax 54: 874-83, 1999) and the inspiratory reserve volume (IRV) (measured for the first time) are also computed. The RV is also compared with the comparable measurements indirectly obtained by subtracting the FVC from the TLC (fRV) and jTLC (jRV).

When raising the lung volume to 30 cm $H_2O$ during an automated lung inflation there are three possible measurements of airway opening pressure (Pao): (1) preset or predetermined airway opening pressure (pPao); (2) airway opening pressure measured while inflation (iPao) is maintained (This is the only one that has been mentioned in the literature during the past ten years. The Pao signal plateau is observed in real time on the computer screen by maintaining a fixed inflating airflow of 15-20 or 12 L/min at 30 cm $H_2O$ until the jacket inflation is triggered); (3) Actual airway opening pressure (aPao) measured as an ensemble average of Pao signal during a 0.20 s airway occlusion after halting the inflating airflow and prior to passive exhalation or activating the jacket inflation. The present invention measures and defines this third airway opening pressure during. RVRTC (FE). Only aPao can reflect the exact pressure within the lungs and airways which in turn determines the measured exhaled lung volume and would therefore facilitate the standardization of raised lung volume measurements.

Infants are obligatory or preferential nose breathers, yet their average nasal resistance (Rn) is 13 cm $H_2O/L/sec$, or nearly 50% of the total airway resistance as in adults. Therefore, maintaining an open mouth during RVRTC from an airway opening pressure (Pao) of 30 cm $H_2O$ ($V_{30}$) is crucial. The higher nasal than the pulmonary airway resistance modulates the forced expiratory flows (FEF %) during a nasal (FEn) forced expiration (FE) which an oronasal (FEo) outlet would resolve. This requires a change in design in order to allow the operator to hold and adjust the infant's head and neck and maintain the mouth open. It is therefore another feature of an embodiment of the present invention that an open mouth is maintained in order to generate an oronasal ($FE_O$) instead of a nasal ($FE_n$) expiration during forced expiration in infants in order to prevent the peak expiratory flow from being stifled by the nose so that the true pulmonary instead of the nasal airway flow limitation would then be revealed in the FEFV curves which in turn would allow a potential bronchodilator response to be detected. The measurement setup is modified to allow the operator to hold the infant's head.

The method of the present invention employs a modified commercial system for nitrogen washout combined with a Custom-made Computer Controlled System (CCCS). The device uses a T-valve unit that allows use of the CCCS and the nitrogen washout from the modified commercial system in unison to measure the described lung volumes and capacities at $V_{30}$ similar to all those measured in adults. The T-valve comprises a pneumatic slide valve, pneumotachometer and mini-balloon valve. The T-valve employs two different bias airflows and has two different internal diameters (flow bores). The unique design of the T-valve allows dual measurements within a single maneuver and further allows for automation of the maneuvers.

The present invention provides the capability of measuring several lung volumes and capacities instead of only the one volume, the dynamic Functional Residual Capacity (dFRC), routinely measured in infants.

The present invention enables a comprehensive assessment of infant lung function. The comprehensive nature of the CITP will tremendously increase the ability to investigate to an unprecedented in-depth the nature, evolution of the early stages of not only the following pulmonary diseases but also chest wall dysfunction and to quantify their severity as well as assess the efficacy of early therapeutic interventions in infants and young children:

Cystic Fibrosis: The CITP could be used as an outcome measure for novel treatments, such as gene therapy and drug treatment.

As a critical outcome measure in Chronic Lung Disease of prematurity (Bronchopulmonary Dysplasia) such as investigating treatments or evaluating neonatal intensive care units (NICU).

Asthma: Epidemiological and Clinical Drug Testing studies in infants.

Evaluating the effects of environmental or chemical exposure.

Routine clinical use for assessing lung function in infants with recurrent respiratory symptoms.

Animal Studies: physiological and mechanistic studies of disease.

Obtaining dual measurements from single maneuvers.

Algorithmic analysis of data and quality assurance for multi-center studies.

These and other features, objects and advantages of the present invention will become better understood from a consideration of the following detailed description of the preferred embodiments and appended claims in conjunction with the drawings as described following:

BRIEF DESCRIPTION OF THE SEVERAL VIEWS OF THE DRAWINGS

FIG. 1D shows the connection between the pneumatic circuit and the forced expiration circuit.

FIG. 4A presents F-V curves before giving albuterol: Passive (pEFV) (_._._.) passive-forced (pFEFV) (----) and, using repeated raised volume rapid thoracoabdominal compressions (RVRTC) with increasing jacket pressures (Pj), the forced (FEFV) (-) expiratory F-V curves from a lung volume raised to an airway opening pressure of 30 cm $H_2O$ generated the inspiratory capacity (IC), slow vital capacity (jSVC) and forced vital capacity (FVC), respectively. FIG. 4B presents F-V curves after giving albuterol: Forced (FEFV) (-) expiratory flow-volume curves.

FIGS. 6A-D are plots of flow (FIGS. 6A and 6B) and Pao (FIGS. 6C and 6D) in two subjects (FIGS. 6A and 6C for the first subject; FIGS. 6B and 6D for the second subject) in the measurement of static (sFRC) functional residual capacity.

FIGS. 9A-F are curves of passive (PEFV) (---), passive-forced (PFEFV) (_._._.) and forced (FEFV) (_) expiratory flow-volume (F-V) from a lung volume raised to an airway opening pressure of 30 cm $H_2O$ generating the inspiratory capacity (IC), slow vital capacity (jSVC) and forced vital capacity (FVC), respectively from infants no. 1, 2, 4, 8, 10 and 15.

DETAILED DESCRIPTION OF THE INVENTION

Figure 1:
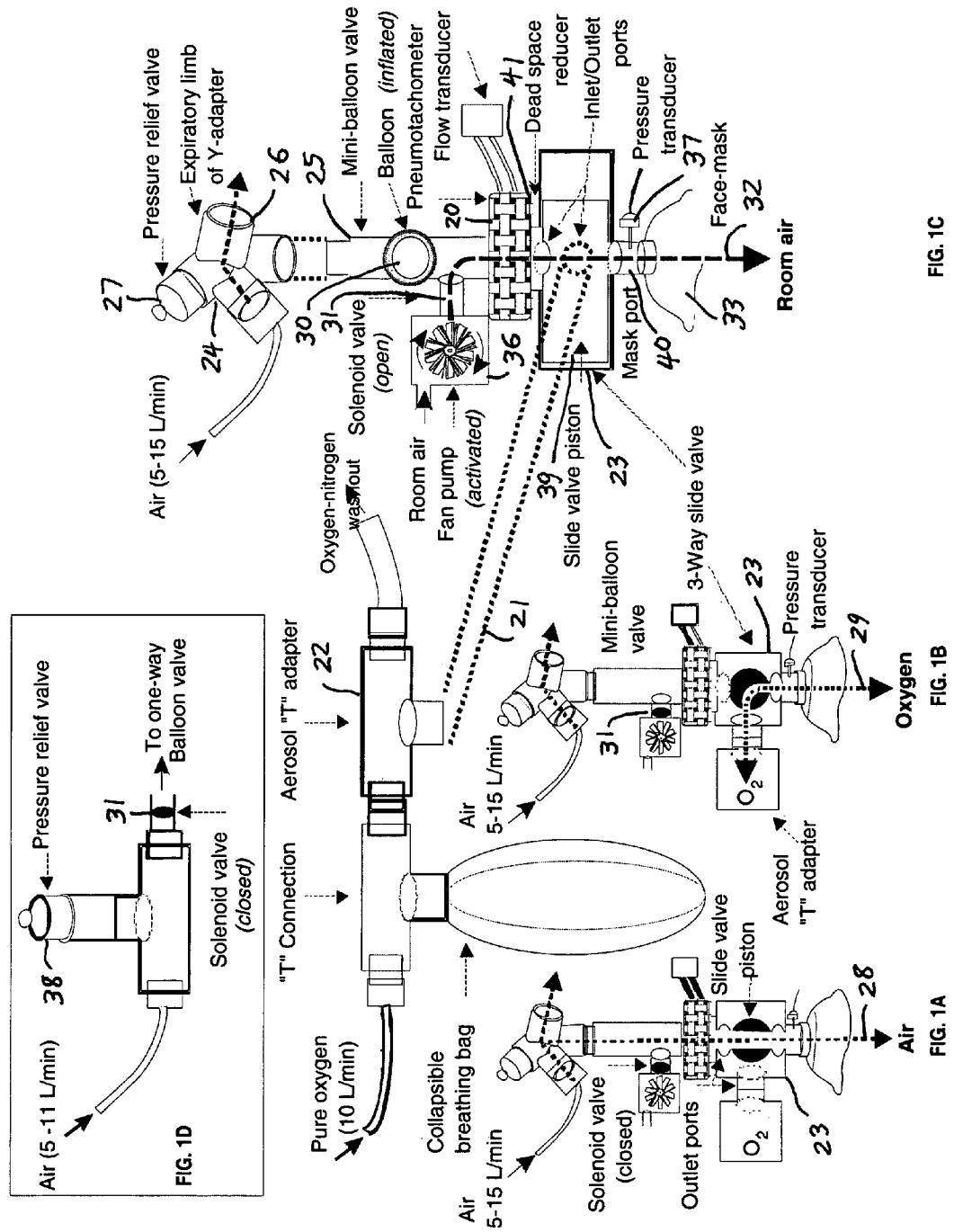
FIGS. 1A-D are diagrams of the T-valve unit and the nitrogen washout circuit: Side views of the circuit in FIGS. 1A and 1B depict the path (arrows interconnected by a dotted line) of air (FIG. 1A) and, after activating the slide valve, of oxygen (FIG. 1B) in and out of the of the infant's airway. The expiration circuit is shown in FIG. 1C.
Figure 2:
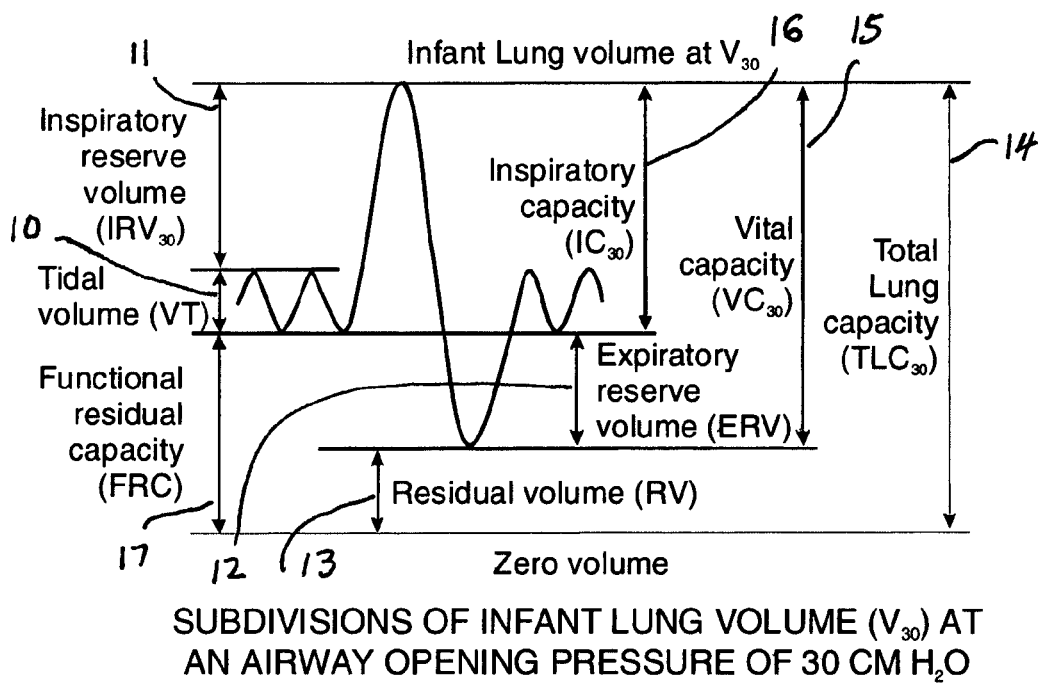
FIG. 2 is a graphical depiction of subdivisions of the infant lung volume ($V_{30}$) at an airway opening pressure of 30 cm $H_2O$.

With reference to FIGS. 1A-9F, the preferred embodiments of the present invention may be described as follows:

In human physiology there are four volumes that do not overlap and four capacities made up of two or more of the primary volumes as shown in FIG. 2. The primary volumes are (1) tidal volume ($V_T$) 10, (2) inspiratory reserve volume (IRV) 11, (3) expiratory reserve volume (ERV) 12 and (4) residual volume (RV) 13. The lung capacities are (1) total lung capacity (TLC) 14, (2) vital capacity (VC) 15, (3) inspiratory capacity (IC) 16 and (4) functional residual capacity (FRC) 17.

Since infants cannot cooperate, we cannot inflate the lungs to their maximum voluntary capacity (since that quantity is unknown) but to a measured mouth or airway opening pressure of 30 cm $H_2O$, which is considered a safe level. Therefore in infants, the second volume would be $IRV_{30}$ 11, and the capacities would be $TLC_{30}$ 14, $VC_{30}$ 15 and $IC_{30}$ 16, respectively. For simplicity the subscript 30 is normally not used herein and volumes and capacities shown without a subscript should be assumed to represent the quantity measured from an airway opening pressure of 30 cm $H_2O$.

When the infant lung is inflated until the pressure measured at the mouth, which is the airway opening pressure (Pao), reaches 30 cm $H_2O$ then the volume is called $V_{30}$ and the entire volume of gas in the lung represents the total lung capacity (TLC) 14. From that level of inflation there are three ways for getting this volume out: (a) The volume that is exhaled entirely passively with just the chest recoil alone is called the inspiratory capacity (IC) 16. (b) The volume by forced expiration by activating a squeeze jacket (j) from the very beginning of the full inflation, that is from $V_{30}$, generates the forced vital capacity (FVC). (As disclosed in U.S. Pat. No. 5,513,647, the disclosure of which is incorporated herein by reference.) (c) Initially passively (slow) then forced with the squeeze jacket being activated during the exhalation which generates the slow vital capacity (jSVC) and the letter "j" indicates that the squeeze jacket was fastened around the infant. After the end of this partial forced exhalation (or jSVC) and with the jacket still inflated the infant may be switched into pure oxygen to measure residual volume (RV) 13 as disclosed in U.S. Pat. No. 6,306,099, the disclosure of which is incorporated herein by reference. The exhaled volume of air generated in (b) and (c) is larger than (a) because the chest is squeezed further beyond its resting recoil.

The present invention provides for the measurement of the static functional residual capacity (sFRC) as follows: after hyperventilation to induce a post-hyperventilation apnea (PHA), after end-passive expiratory switching of the inspired gas from room air to 100% oxygen before the infant resumes his/her spontaneous breathing the remaining gas in the lungs is measured by nitrogen washout. This measurement may be performed in one maneuver with the IC measured also. The total lung capacity (TLC) is calculated as the sum of IC and sFRC. And when you subtract the RV from the TLC you get the "true" slow vital capacity (SVC): TLC−RV=SVC (Note that the jacket is not fastened around the infant when the IC and the sFRC are measured, therefore it is called simply SVC.)

The apparatus used in the present invention is a combination of a Custom-made Computer-Controlled Infant Lung Function System (CCCS) and a modified form of a commercially available apparatus for performing the bias flow nitrogen washout technique. The apparatus rapidly raises the lung volume of an infant, prior to generation of a forced expiratory flow. For accurate measurements, all volumes into and out of the infant must be accountable and the system must be leak free.

With reference to FIGS. 1A-D and 3, the nitrogen washout apparatus, modified from a commercial system, the Pediatric Pulmonary Unit (PPU) 2600 (SensorMedics, Anaheim, Calif., USA), is used to measure FRC and RV. In the PPU, the expired gas enters a mixing chamber that is connected via a precision needle valve and a vacuum pump to an $N_2$ analyzer, and the $N_2$ concentration is integrated electronically by the PPU signal processing system. The CCCS is used to perform RVRTC and to adapt the PPU for measuring the FRC, RV, TLC and jTLC in several ways: (1) to introduce a pneumotachometer (PNT) 20 into the circuit while the infant is breathing room air in order to measure the expired gas volume from $V_{30}$ by integrating the flow signal to produce volume; (2) to display signals (flow, Pao, jacket pressure (Pj) and flow-volume loops) in real time on a computer monitor screen (not shown) to enable timely initiation of the nitrogen washout.

FIGS. 1A-D are diagrams of the T-valve unit and the nitrogen washout circuit: In FIG. 1C, the long parallel dotted lines 21 point to the connection site of the central port of the aerosol "T" adapter 22 which carries a fixed 10 L/min bias flow of oxygen into the inlet/outlet port of the slide valve 23. When measuring the inspiratory capacity (IC) with the static functional residual capacity (sFRC) and the slow vital capacity (jSVC) with the RV, Y adapter 24 is connected to balloon valve 25. The infant is hyperventilated until a post-hyperventilation apnea (PHA) is induced by intermittently occluding the expiratory limb 26 of the Y adapter 24 which diverts air to the infant through the pneumotachometer (PNT) 20, raising the lung volume to an airway opening (Pao) pressure plateau set at 30 cm $H_2O$ by the pressure relief valve 27. Side views of the circuit in FIGS. 1A and 1B depict the path (arrows interconnected by a dotted line) of air 28 (FIG. 1A) and, after activating the slide valve 23, of oxygen 29 (FIG. 1B) in and out of the of the infant's airway. Note that the infant breathes in and out of the PNT 20 when measuring the IC and jSVC but after the slide valve 23 switches the infant into oxygen, he/she no longer breathes through the PNT 20.

Figure 3:
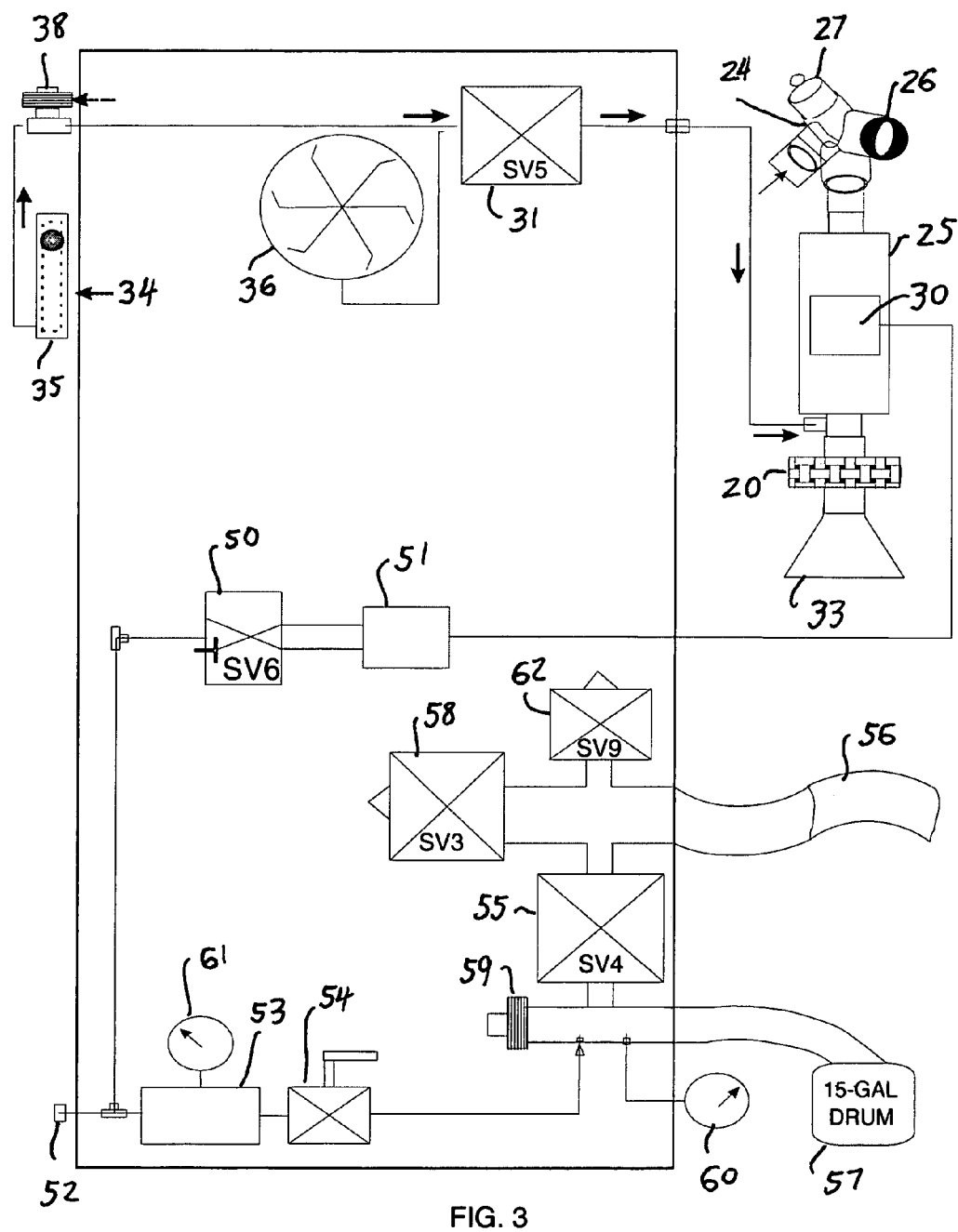
FIG. 3 is a block diagram of the pneumatic circuit.

The forced expiration circuit is shown in FIGS. 1C and 3. Once a PHA is induced as above, automated raised volume rapid thoracoabdominal compression (RVRTC) proceeds as follows: (1) the balloon 30 within the mini-balloon valve 25 is inflated; (2) the solenoid valve 31 opens and airflow is delivered to the lungs (dotted line arrow 32 exiting the facemask 33) from a pneumatic circuit either using a medical wall air source 34 via a high-precision flowmeter 35 or an impeller pump 36 raising the lung volume until the preset Pao (30 cm $H_2O$) sensed by the pressure transducer 37 is attained, (3) the inflating airflow is halted, the solenoid valve 31 closes and the balloon 30 remains inflated for 0.20 s occluding the infant's airway, (4) the squeeze jacket (j) (not shown) is activated but deflation of balloon 30 is delayed for another 0.05 s and (5) forced expiration proceeds. Note that the infant breathes in and out of the PNT 20 during the RVRTC. Once the inflating airflow is adjusted to the infant's size, the pressure relief valve 38 within the pneumatic circuit is precisely adjusted to release pressure at 32 cm $H_2O$ using the calibrated airway opening pressure transducer 37 inserted into the circuit port when the latter is plugged after disconnecting the transducer shown in FIG. 1D.

The "T-valve" unit is made of three components as shown in FIGS. 1A-C: (1) a pneumatic three-way slide valve 23 (length 12.7 cm) designed to be leak-free and to not allow gas mixing between ports while the piston 39 is sliding (2) a 0-160 L/min heated screen pneumotachometer (PNT) 20 and (3) a one-way mini-balloon valve 25. The mask port 40 of the slide valve 23 is connected to the appropriate size 0, 1 or 2 transparent face mask 33 (Rendell-Baker Soucek pediatric face mask; Gary Hull Anesthesia, Huntington Beach, Calif., USA) which is held onto the infant's face with silicone putty (Theraputty; North Coast Medical Inc. San Jose, Calif., USA) and an airtight seal is achieved. The T-valve allows combined measurements of static and dynamic lung volumes at $V_{30}$ to be performed by using the PPU and CCCS in unison. The dead space volume (DSV) is minimized significantly when the infant is breathing room air by using a mini-balloon valve 20 (DSV) (13.73 ml) instead of a regular sized balloon valve and discarding the slide valve outlet port and using only the body of the PNT 20 without its two port tubes. One end of a dead space reducer 41 (DSV, 1.4 ml) screws directly into the outlet opening of the slide valve 23 and its other end into the body of the PNT 20. The opposite end of the body of the PNT 20 screws directly onto a customized end of the mini-balloon valve 25. This custom end is also connected via a 0.5-inch connection to a solenoid valve 31 in the CCCS that allows the infant's lungs to be inflated to a predetermined Pao (pPao) of 30 cm $H_2O$ ($V_{30}$).

The straight-through path within the T-valve (FIG. 1A), which has a 27.83 ml DSV and a constant flow-bore of 13.97 mm ID and which extends from the mask port 40 of the 3-way slide valve 23, through the slide valve piston 39, the slide valve outlet opening, the dead space reducer 41, the PNT 20 and the mini-balloon valve 25, is used when the infant is breathing room air and during manual hyperventilation. The DSV from the mask port 40 to the lower edge of the opening of the 0.5-inch connection is 18.67 ml, which is the path of the airflow inflating the lungs when the solenoid valve 31 opens.

The perpendicular path through the T-valve is used for nitrogen washout (FIGS. 1A-B). It has a 8.27 ml DSV and a 9.52 mm flow bore and extends from the mask port 40 of the 3-way slide valve 23 through the slide valve piston 39 and perpendicular outlet port through the aerosol "T" adapter 22 to a circuit carrying a precisely adjusted doubly-checked constant bias flow of 10 L/min pure oxygen for all infants weighing>5 kg. The slide valve piston 39 switches the infant into pure oxygen to initiate the nitrogen washout shifting from one position to the other in 0.25 s.

Although the RVRTC is sometimes performed with the entire T-valve assembly, it is preferable, especially for small infants, to disconnect the slide valve 23 and the dead space reducer 41 from the assembled mini-balloon valve 25 and PNT 20 and screw to the latter the PNT port tube fitted with a ⅛ inch port to connect the pressure transducer 37. This mini-balloon valve/PNT/maskport tube assembly is 12.8 cm long, has a DSV of 23.0 ml and a 13.97 mm flow bore. The DSV from the PNT maskport tube to the lower edge of the opening of the 0.5-inch connection is 11.0 ml which is the path via the solenoid valve of the airflow inflating the lungs.

The pneumatic circuit is shown in FIG. 3. In one embodiment, the infant's lungs are inflated using air drawn from room air into the pneumotachometer (PNT) 20 by the impellor pump 36. The inflation cycle is controlled by opening solenoid valve 31 while keeping solenoid valve 50 closed. A prototype impeller pump 36 used a high quality brushless DC motor (Cat. No. EC032-060-33-EBB200B, Maxon Motor, Sachsein, Switzerland) with a Maxon electronic commutation speed control (Cat. No. MMC-EC050046-05P300A) in order to (1) provide a high speed rotation of the impellor to minimize pressure pulsations and (2) to prevent electrical interference. The impeller blades are derived from a commercial mattress inflation pump (Inflate-all, Coleman Co. Inc., Wichita Kans., USA).

The impeller pump 36 provides pressures between 30 and 33 cm $H_2O$ into a closed circuit and flows in excess of 120 L/min into an open circuit when the rated DC voltage (24 VDC) is applied to the pump motor. The electrical interference is negligible. The flow is smooth enough that filtering of the flow signal is not necessary. Although a purpose-built impeller pump is described herein, any type of pump having similar characteristics may be used in the practice of the present invention. For example, the Neopuff™ Infant Resuscitator made by Fisher & Paykel Healthcare Corporation Limited would be acceptable.

Air intake to the impeller pump 36 is provided from ambient room air. Air outflow is then passed via solenoid valve 31 when open and with the balloon 30 of the one-way balloon valve 25 inflated by solenoid valve 50, through the pneumotachometer (PNT) 20 and facemask 33 inflating the infant's lung to the predetermined airway opening pressure (Pao) of 30 cm $H_2O$. Inflation is then halted by solenoid valve 31 and the impeller pump 36 is inactivated once this Pao is attained. The PNT 20 is located at the proximal end of the one-way balloon valve 25 close to the infant's mouth and away from the bias flow of air used to hyperventilate the infant via the Y-adapter 24 prior to RVRTC. This location of the PNT 20 accomplishes the critical goal of reducing the noise in the flow signal that occurs when the PNT 20 is located close to the bias flow of 15 L/min air. A Pao of 30 cm $H_2O$ is easily attained in infants and young children up to 3 years of age. From a safety aspect, the unit still provides maximum lung inflation pressures of only 30-33 cm $H_2O$.

An alternative embodiment of a pneumatic circuit provides an external source of air for the last automated lung inflation via solenoid valve 31 instead of the impeller pump 36. The alternative circuit consists of a constant bias airflow (range 5-15 L/min) from a medical grade wall air source 34 via a high precision flowmeter 35 that allows fine adjustments of the airflow which varies according to the infant's age. As a safety measure, a pressure relief valve 38 is incorporated into the pneumatic circuit that releases pressure at 32 cm $H_2O$ or so.

Compared to the impeller pump 36, the use of the pneumatic circuit with a constant bias airflow from a medical wall air source via a high precision flowmeter to perform the automated last lung inflation has two important advantages: (1) It is far less disturbing to the sleeping infant that the impeller pump 36 which often startles a lightly sedated sleeping infant at the time of jacket activation causing motion induced transient artifact in the FEFV curve; and (2) It enables very fine adjustments of the inflating airflow such that not only the actual Pao attained was closest to the pPao by fewer RVTRC maneuvers were needed to achieve the optimum inflating airflow for the individual infant. It is important to note the difference between the two airflows used: (1) The constant bias airflow circulating through the Y-adapter, which is intended for manual hyperventilation, is adjusted according to the infant's size, age, depth of sedation, tidal breathing pattern and tolerance, and the clinical suspicion of the presence of a large airway malacia; relying on a robust PHA, (2) The pneumatic circuit airflow is adjusted differently, slightly lower, to only generate a gentle but rapid automated last lung inflation designed to achieve an aPao closest to 30 cm $H_2O$.

Solenoid valve 31 is a Model SCD210C94 1 inch pipe (1-inch orifice), normally closed operation, brass bodied valve manufactured by ASCO (Automatic Switch Company, New Jersey, USA). Brass bodied valves are selected for their reliability and leak free operation. DC operating coils are used on the solenoid valves and all solenoid valves are placed inside the enclosure.

A commercial (Hans Rudolph, Kansas City, Mo., USA: Model CR1154: A Model 9340) 2-way balloon valve 25 with modified inlet and outlet ports and modified to accept tubing above and below the valve for connection to the pump system is used. The balloon valve 25 is operated by a double piston pump assembly 51 (Hans Rudolph, Kansas City, Mo., USA Model 174000) that is controlled by high-pressure medical wall air 52 (400 kPa) from a two-position four-way solenoid valve 50 (ASCO-Jucomatic Model 263-00-015-77). The balloon valve 25 when activated displaces a volume of air just sufficient to inflate the balloon 30 properly. There is no pneumatic coupling from the high pressure side to the balloon 30. The driven side is rod coupled to the piston. As a result there is no chance of excessive volume or pressure being delivered to the patient. The pressure within the air circuit used to inflate the jacket 56 is reduced to a safe level (40 kPa) by a pressure regulator 53. When the manual ball valve 54 is closed, the jacket inflation circuit is completely isolated from the 40 kPa-air source.

Once the inflating airflow is adjusted to the infant's size, a safety pressure relief valve 38 incorporated in the pneumatic circuit is adjusted to release pressure at 32 cm $H_2O$ or so using the calibrated Pao transducer 37 inserted into a circuit port, then the latter is plugged after disconnecting the transducer 37 (FIG. 1D).

The mask port 40 of the 3-way slide valve 23 is 20 mm long, has a 22 mm outer diameter (OD)×13.97 mm inner diameter (ID) and is fitted with a ⅛" port which is connected to the pressure transducer 37 to measure Pao.

The sequence of valves is controlled by BRATLAB software (RHT-INFODAT, Montreal, Quebec, Canada) on computer (Compac PC) (not shown). The computer sends byte wide logical signals to the interface circuit of the equipment to simultaneously set the state of up to 8 devices (seven solenoid valves and one pump). The parallel digital input/output card used to provide this function is a model PC-36B (Eagle Technology, Cape Town, South Africa). The digital signals from the PC-36B are fed to a custom designed interface, which is used to drive the DC solenoids and pump. All signals are collected and analyzed on the CCCS computer with the LABDAT-ANADAT 5.2 data acquisition and analysis software (RHT-INFODAT). The measurement system consists of external flow and pressure measuring devices interfaced to a computerized data acquisition, analysis and control system. Parameters monitored are mouth pressure, jacket cuff pressure and flows to and from the patient. Flows are integrated under software control to determine volumes. Data acquisition is performed by an analog to digital data acquisition board (Data Translation, MA, USA) capable of simultaneously acquiring up to 8 differential input channels.

A four-limb Y-adapter 24 is connected to the distal end of the mini-balloon valve 25 to perform manual hyperventilation and induce the PHA when performing RVRTC and measuring the sFRC and RV (FIGS. 1A-D). The Y-adaptor 24 carries a constant bias flow of air at 5-15 L/min. A pressure relief valve 27 embedded in one of the four limbs of the Y-adapter is precisely adjusted to release pressure at 30 cm $H_2O$ at the bias airflow rate tailored to the infant's size (range, 5-15 L/min).

Forced expiratory flow-volume curves are generated by inflating the jacket 56 surrounding the infant's chest and abdomen using solenoid valve 55, which is connected to a large gas reservoir 57 (15 gal. drum) that is manually filled via a ball-valve 54 to a suitable pressure. The jacket 56 is deflated using solenoid valve 58. Internal volume of the delivery system is kept as small as possible (short tubing, etc.) within the limits of flow limitation (using wide bore tubing so as not to limit flow).

The drum 57 is filled from a 400 kPa wall supply of medical air 52. The pressure is reduced to a safe level (40 kPa) by a pressure regulator 53. A safety pressure relief valve 59 set to release pressure at 16 kPa is also provided inside the enclosure of the filling system. The filling of the drum 57 is controlled by a hand activated ball valve (Whitey® type B-43F4) 54. The filling pressure is monitored by an analog pressure gauge (VDO®, 0 to 16 kPa range, Part No. C553 564 006) 60 mounted, externally to the enclosure. Therefore, once the drum 57 is filled to the desired pressure level and the ball valve 54 is manually turned back to the closed position the infant is completely isolated from the high pressure source when jacket inflation is activated. The drum 57 is a commercial 15-gallon "Tight Head Drum" (Basco o, University Park, Ill., USA). Its top accepts a large rigid hose, through which the drum 57 is filled and its contents dumped to the jacket 56. The drum 57 was tested up to 30 kPa without rupture.

Solenoid valve 55 dumps pressure from the drum 57 to the squeeze jacket 56 under computer control. Solenoid valve 55 is a model D210B54 1-inch pipe (1 inch orifice), normally closed operation, brass bodied valve manufactured by ASCO (Automatic Switch Company, New Jersey, USA). A 1 inch valve was selected as the smallest acceptable valve to provide fast enough dumping of the gas from the drum 57 to the jacket 56. Larger valves were much more expensive and had slower closing and opening characteristics.

The gas is vented from the jacket 56 to the atmosphere by solenoid valve 58. SV3 is a Model SCD210C34 1-inch pipe (1-inch orifice), normally open operation, brass bodied valve manufactured by ASCO (Automatic Switch Company, New Jersey, USA). A normally open valve was selected so that the jacket 56 would be automatically deflated in the event of a power or actuator coil failure.

Redundant measures prevent over-pressurization of the reservoir drum 57. The filling supply pressure is regulated to a safe level (40 kPa, which would not exceed the drum rupture pressure) by a pressure regulator (Norgren, Warwickshire, England: Part No. R07-200-RNAG) 53 fitted with a 0–100 kPa pressure gauge (VDO®, Part No. C410 569 006) 61.

A safety pressure relief valve 59 is provided inside the enclosure of the filling system. The pressure relief valve 59 is a modified AMBU PEEP® valve, Part No. 000 213 000. The relief pressure of the valve 59 is modified from its nominal 20 cm $H_2O$ to 20 kPa by replacing the main spring. The valve with its 32 mm inlet begins dumping at about 20 kPa and keeps the pressure below 40 kPa when the hand ball valve 54 is left wide open into a closed circuit.

The drum 57 has only one inlet and outlet. It is not possible to fill from any source other than the equipment being described and still dump to the squeeze jacket 56. Filling of the drum 57 is via a rigid hose and the pressure release valve 59 is set to pop off at 16 kPa. A second dump valve 62 is added to the jacket deflation circuit. Valve 62 operates in order to dump the jacket pressure in the event that solenoid valve 58 remains closed (i.e. jacket inflated) for longer than 30 seconds. Control is independent of the computer control system.

The balloon valve 25 is always disconnected from the facemask 33 left on situ on the infant's nose and mouth and a cannula carrying a constant flow of 2 L/min air is inserted into the facemask port 40 after each respiratory maneuver to provide fresh air to the sleeping infant and eliminate carbon dioxide accumulation.

A large, manually operated, mushroom safety switch is provided on the outside of the enclosure in order to de-activate all solenoid valves in the event of computer control circuit failure.

Flows are determined using a Hans Rudolph® heated pneumotachometer 20 flow head Model 4700. This unit has a calibrated flow range of 0-160 L/min. The differential pressure developed across the pneumotachometer 20 is amplified and filtered to produce the flow signal delivered to the computer data acquisition board. The system uses a 4 channel signal conditioner system Model SC-14 manufactured by Meakins-Christie Laboratories (McGill University, Quebec, Canada). This system uses Omega (Stamford, Conn., USA) pressure transducers Models PX170-07GV and PX170-07DV. Pneumotachometer heating is provided by the power supply for the SC-14. The manufacturer is SCIREQ Scientific Respiratory Equipment Inc., 6600 St-Urbain, Suite 300, Montreal, QC, H2S 3G8, Canada.

A digital manometer is used to calibrate the pressure transducers (range 0-125 cm $H_2O$; Dwyer Instruments Inc., Michigan City, Ind., USA). Since the protocol of the present invention employs a wide range of flow rates, the piston of a calibrating syringe (Hans Rudolph Inc.) is used to calibrate the PNT 20 by injecting and withdrawing 200 ml using a wide range of flows in 10-15 simulated breaths. The flow signal is integrated to produce volume whose mean differed by less than 0.5% from the known volume.

When the facemask 33 is connected to the slide valve mask port 40, the combined obligatory DSV of the connected ports is 10 ml. The mask deadspace is minimized significantly by placing extra putty under the mask and along the sides of nose such that only 1-4 ml above the obligatory deadspace of 10.0 ml remains that could easily be estimated visually, i.e. range 10-14 mL for the mask and apparatus. Volume is corrected for the effective dead space of the face mask and the slide valve port and converted to BTPS (Body Temperature, Pressure and Saturation corrections).

The inspiratory capacity (IC) and the static (sFRC) (passive) functional residual capacity are measured as follows. With the squeeze jacket 56 unfastened, several rapid inflations are delivered to the infant lungs by intermittently occluding the expiratory limb 26 of the Y connection 24 (FIG. 1C) until a PHA is induced. The last manual lung inflation (i) is maintained until a Pao plateau (iPao) is primarily observed at $V_{30}$ and the inspiratory flow (F) ceases to rise in real-time on the CCCS computer monitor screen, then the occlusion of the Y-adapter's expiratory limb 26 is terminated. Passive expiration from $V_{30}$, which is entirely driven by the inward elastic recoil of the chest wall, is allowed to be completed passively by closely watching the flow signal and the flow-volume loop. The (passive) expiratory time (tpE) is recorded. The slide valve 23 is activated after end-passive expiration during the post-expiratory pause, switching the infant to breathing 100% oxygen (FIG. 1B) before he/she resumes spontaneous inspiration to measure the sFRC. When a 0% nitrogen concentration is displayed on the PPU monitor, the slide valve 23 is activated and the infant is switched back to breathing room air (FIG. 1A). Thus, from a single (IC-sFRC) maneuver the IC is measured by integrating the flow signal to produce volume and the sFRC with the sum being the TLC. Furthermore, several 20-second epochs of the tidal breathing are routinely recorded in the same infant. Therefore, when the average of the measured tidal volume ($V_T$) is subtracted from the IC, the inspiratory reserve volume (IRV) (measured for the first time) is obtained.

FIGS. 6A-D illustrate the measurement of the static (sFRC) (passive) functional residual capacity. FIGS. 6A and 6C illustrate one subject and FIGS. 6B and 6D illustrate the second subject, both zooming on the time period that begins with end passive expiration of the last lung inflation at 1.18 s and 1.98 s and ends at 16.2 and 14.2 s of the data collection period, respectively. Each includes a trace of flow (FIGS. 6A and 6B) and airway opening pressure (Pao) (FIGS. 6C and 6D). In these plots, inspiration is positive and expiration is negative. End-passive expiration begins when flow and Pao are zero signalling the onset of the post-hyperventilation apnea (PHA). The slide valve switching the infant into the bias flow of oxygen can be seen at 7.78 and 8.39 s, respectively, causing an abrupt upward shift in baseline of the Pao tracing from zero to about 0.57 cm $H_2O$. The latter is caused by the continuous positive Pao generated by the constant bias flow of $O_2$. Note that after switching the infant into oxygen he/she no longer breathes through the pneumotachometer. Pao remains at 0.57 cm $H_2O$ signalling apnea. This PHA is followed by the onset of the first negative deflection (inspiration) in Pao at 15.7 and 10.5 s, that is 7.92 and 2.11 s after switching the infant into $O_2$, respectively, indicating the onset of the $N_2$ washout. The total duration of the PHA is about 14 and 8.25 s, respectively. The latent period before the rise above baseline of the $N_2$ washout curve recorded in real time from the computer screen was about 8 and 4 s, respectively.

The slow vital capacity (jSVC) and residual volume (RV) are measured using the technique disclosed in U.S. Pat. No. 6,306,099. After inducing a PHA manually, RTC is initiated during the last passive expiration from $V_{30}$. The RV is estimated by measuring the volume of nitrogen expired after end forced expiratory switching of the inspired gas from room air to 100% oxygen while jacket inflation is maintained at the time of switching into oxygen during the post-expiratory pause. Thus, from a single (jSVC-RV) maneuver another measurement of the slow vital capacity (jSVC) is obtained by integrating the flow (F) signal to produce volume and the RV is obtained by nitrogen washout with the sum being the jTLC. This enables a determination whether the fastened jacket 56 has restricted the chest wall expansion and vital capacity.

The raised volume rapid thoracoabdominal compression (RVRTC) technique is used to obtain FVC. Following the induction of the manual PHA, the automated RVRTC is performed from $V_{30}$ (FIGS. 1A-D) as follows: Using the high precision flowmeter 35 flow-control knob, the constant bias airflow (5-12 L/min) within the pneumatic circuit is finely pre-adjusted relative to the infant's size to deliver the last lung inflation when the solenoid valve 31 opens with a stroke of the computer's keyboard followed by automated RTC. When used, a rheostat modifies the impeller pump speed to adjust the inflating airflow rate. A combined adjustment of the inspiratory airflow rate relative to the infant size and the pPao value entered on computer up to a fraction of one cm $H_2O$ above 30.0 is necessary in order to obtain and reliably measure a "true" actual Pao (aPao) as close as possible to 30.0 cm $H_2O$ during the last automated lung inflation after halting the inflating airflow when the pPao is attained and then maintaining an airway occlusion for 0.20 s before activating the jacket inflation. The software computes the aPao by ensemble averaging of the Pao signal over this 0.20 s occlusion period. The automated lung inflation is triggered in most infants during the early portion of the passive expiration of the last manual inflation which facilitates the attainment of an aPao significantly close to 30.0 cm $H_2O$. Alternatively, once the PHA is induced by manual hyperventilation, one computer keyboard stroke could trigger two lung inflations to the pPao separated by a short expiratory time of 0.5 sec (breath stacking) and automatic activation of jacket inflation when the second lung inflation attains the pPao as described above. Although the automatic jacket inflation is triggered at the end of the 0.20 s airway occlusion, the expiratory valve opens after a fixed preset time delay of 0.05 s. The RVRTC is repeated using increasing Pj until flow limitation is achieved. The aPao, the average Pj plateau and the forced expiratory time (tFE) are obtained from recorded signals.

The T-valve allows dual measurements in a single maneuver in which there is a continuum between the dual measurements and interdependence in switching.

For example, during the IC-sFRC maneuver when measuring the inspiratory capacity the infant starts passive exhalation from $V_{30}$. The pneumotachometer records flow which is integrated to compute the volume. If one waits until complete exhalation the integrated volume equals the inspiratory capacity (IC) and if the slide valve is switched after end-expiration so that the infant is now breathing the pure oxygen, the remaining gas volume measured by the nitrogen washout will equal the sFRC. Suppose now that the operator made a mistake and switched the infant into the pure oxygen before end-expiration. The result would be that the integrated volume by the pneumotachometer would be a slightly underestimated IC. Consequently the volume measured by $N_2$ washout would be a slightly overestimated sFRC (because it has the added non-exhaled volume remaining from the passive expiration).

Similarly, during the jSVC-RV maneuver, if the correct jacket pressure is used, the exhaled flow integrated by the pneumotachometer will equal the jSVC and when the slide valve switches the infant into the pure oxygen while the jacket is still inflated, the volume measured by $N_2$ washout will equal the RV. Suppose now that the operator had used a low jacket pressure, the result would be that the integrated volume by the pneumotachometer would be a slightly underestimated jSVC and a slightly overestimated RV.

Therefore, the two volumes measured in a single maneuver are interdependent. If the first one measured by the pneumotachometer is erroneously small then the second one measured by $N_2$ washout will be erroneously higher than its true value and vice-versa. However, the total volume in either case will be the same, i.e., the total lung capacity (TLC).

In summary, when the infant exhales from $V_{30}$ through the T-valve, the latter will measure in a single maneuver two gas volume components of the exhaled gas that together will add up to obtain the TLC, which could remain accurate even if both components were not: the first component through the pneumotachometer and the second component which remains in the lung after end-expiration, indirectly by the $N_2$ washout:

| | First Component | Second Component |
|---|---|---|
| 1. | Passive exhalation alone = IC | sFRC |
| 2. | Passive then completed with partial forced expiration = jSVC | RV |
| 3. | RVRTC = Forced vital Capacity (FVC) | RV (must be automated) |

In order to achieve this continuum between measurements in each of the three maneuvers summarized above, the T-valve is designed with a mini-balloon valve to minimize dead space and a pneumatic slide valve. The pneumotachometer is placed between the pneumatic slide valve and the mini-balloon valve in order to minimize the noise from the constant bias flow circulating through the Y-adapter on the zero flow signal baseline of the pneumotachometer since the latter is placed away from the bias flow and this distance is created by the 'length' of the mini-balloon valve.

Since the pneumotachometer is also closer to the infant's airway opening, the heart beats are sensed by the pneumotachometer and can be counted by analyzing the flow signal baseline. As shown in FIGS. 6A-D, zooming enhances tiny waves in the flow trace zero baseline that disappear once the infant is switched into $O_2$ at 7.78 and 8.39 s, respectively, since his/her airway opening is no longer exposed to the pneumotachometer during the ongoing apnea. These waves are caused by the rhythmic myocardial relaxations and contractions causing minute compressions and decompressions of the contiguous lungs and airways generating miniscule changes in airflow that are transmitted to the airway opening and the PNT. The number of miniscule peaks within the period from 1.47 to 6.98 s is 9 and from 1.78 and 8.39 s is 14 that corresponds to a frequency of 1.63 Hertz or 98 per min and 2.12 Hz or 127 beats per min which is comparable to the monitored heart rate of 100 and 128 per min, respectively, by the pulse oximeter.

It is also important for the functioning of the T-valve that dead space is reduced as much as possible. This is especially the rule in infants because of their small size and the small size of their breath volume. They must not be allowed to "recycle" or breathe their own exhaled air which has less oxygen and more carbon dioxide. A small dead space allows fresh air to be accessible during each successive breath.

In the prototype described herein, once the slide valve switches the infant into the pure oxygen to begin the $N_2$ washout, he/she will be breathing in and out until the $N_2$ washout is completed (1 minute or so in the healthy and 3-4 minutes or more in the infant with lung disease) through the perpendicular path that has a dead space volume of only 8.27 ml and which is much smaller than that of the straight-through path which is 27.83 ml.

It is also significant that the T-valve allows two different bias airflows as described above.

Also significant to the functioning of the T-valve is that the straight-through path within the T-valve has a constant flow-bore of 13.97 mm ID which was designed to be equal to that of the pneumotachometer in order keep the flow stable and hence measurements accurate. The smaller bore of the perpendicular path helps reduce the dead space volume as described above.

Occluding the airway for 0.02 s can be used in all three maneuvers previously described. When measuring the inspiratory capacity, instead of raising the last lung inflation manually to an airway opening pressure of 30 cm $H_2O$ ($V_{30}$) as described, this step could be automated, The lung is inflated to 30 cm $H_2O$, flow is halted, and the airway occluded for 0.02 sec followed by passive expiration when the balloon within the mini-balloon valve deflates. The jacket is not used in this setup.

The 0.02 s occlusion step may be used when measuring the jSVC by manually inflating the lung followed by passive expiration and the jacket inflated via a computer keyboard stroke during the passive expiration. It could be automated also with the machine raising the last lung inflation, the 0.02 s occlusion followed by passive expiration as described above with respect to the inspiratory capacity, and the jacket activated either automatically or via a computer keystroke (manually) during the expiration to measure the jSVC. Then the slide valve could be switched automatically or via a computer keyboard stroke (manually) after end-expiration before the jacket deflates to measure the RV by $N_2$ washout.

In the third maneuver, the 0.02 s occlusion step may occur when measuring forced expiration and forced vital capacity by RVRTC as described previously.

Infants are obligatory or preferential nose breathers and have a higher nasal than pulmonary airway resistance. Therefore, maintaining an open mouth during RVRTC from an airway opening pressure (Pao) of 30 cm $H_2O$ ($V_{30}$) is crucial. An opened mouth sometimes unexpectedly closes or becomes obstructed by putty during testing and a lightly sedated infant often actively closes his/her mouth towards the end when oral sucking movements became more active which necessitates replacement of the mask and putty after re-opening the mouth when the infant relaxes back into sleep. Therefore, it is essential to inspect the mouth through the mask port before and, along with the peak flow of the FEFV curve generated, after each RVRTC. The disappearance in real-time on the computer monitor screen of the prominent peak of maximum flow in the passive flow-volume loops during the hyperventilation is a useful clue that the mouth has closed and the maneuver has to be aborted.

Published studies to date have not emphasized the importance of or reported whether an open mouth had been maintained and monitored during the RVRTC or not. Although the potential for a $FE_n$ to modulate FEF and impact the bronchodilator response in infants has long been suspected, the magnitude of the problem and its impact on ILFT studies have remained elusive. Actually, following repeated RVRTC maneuvers it would be plausible for an inexperienced investigator to ascribe progressive stifling of the PF in the FEFV curves to gastric gaseous distension, a paradoxical response to an administered bronchodilator drug or even a delayed jacket activation, not realizing that the mouth was closed or increasingly getting obstructed by putty thus increasing the nasal airways' contribution to the forced expiration ($FE_n$). Therefore, the mouth and nares must be visualized through the mask port and along with the generated FEFV curve after each RVRTC.

The clear facemask embedded in firm putty is a must because it maintains the infant's mouth open and, while an assistant initiates automated RVRTC via the computer keyboard, the investigator who performs the manual hyperventilation may adjust and, if the generated FEFV curve exhibits flow transients from glottic closure, re-adjust the head and neck and apply minimal pressure on the mask to prevent airleaks while simultaneously performing a coordinated gentle anterior thrust on the lower jaw to decrease upper airway resistance by increasing the oropharyngeal cross-sectional area to facilitate a $FE_o$ that generates smooth FEFV curves with prominent peaks of maximum flow. This could not be accomplished with air-filled cushioned masks because of frequent airleaks. For older toddlers and very small infants, the assistant may sit by the infant's head and apply gentle pressure on the infant's cheeks to keep the mouth open, adjust the head and neck, perform the jaw thrust and support the valve assembly while the investigator performs the manual hyperventilation and initiates RVRTC via the keyboard.

The valve assembly must never be held via a mechanical arm connected to the facemask kept in situ on the infant's nose and opened mouth via the firm putty during testing. The likelihood of regurgitation of gastric contents with potential aspiration is greater with the raised than tidal volume measurements and definitely with an opened mouth which hinders swallowing.

Infant pulmonary function setups whose design does not enable the investigator(s) to easily reach, hold and adjust the infant's head and neck and maintain an open mouth during RVRTC are likely to facilitate the generation of a $FE_n$ rather than a $FE_o$. Moreover, in aiming at preventing airleaks around the facemask, the use of a mechanical arm to support the facemask in situ on the infant's face and nose would likely exert pressure on the lower jaw which diminishes the oropharyngeal cross-sectional area and modulate the forced expiratory flows.

Although natural breathing is sufficiently sustained via the nose and rarely shared between the mouth and nose in healthy infants, the known higher nasal than the pulmonary airways resistance unequivocally modulates raised lung volume forced expirations in infants by stifling peak flow and could inevitably mask a potential bronchodilator response. Therefore, a clear facemask applied around the infant's mouth and nose with a layer of putty to achieve an airtight seal during infant lung function testing is inadequate for the raised volume rapid thoracoabdominal compression (RVRTC) without an opened constantly monitored mouth and a gentle anterior lower jaw thrust that ought to be integral to this sophisticated technique in order to generate an oronasal rather than a nasal forced expiration so that the flow limitation achieved would be in the pulmonary instead of the nasal airways.

Figure 4A:
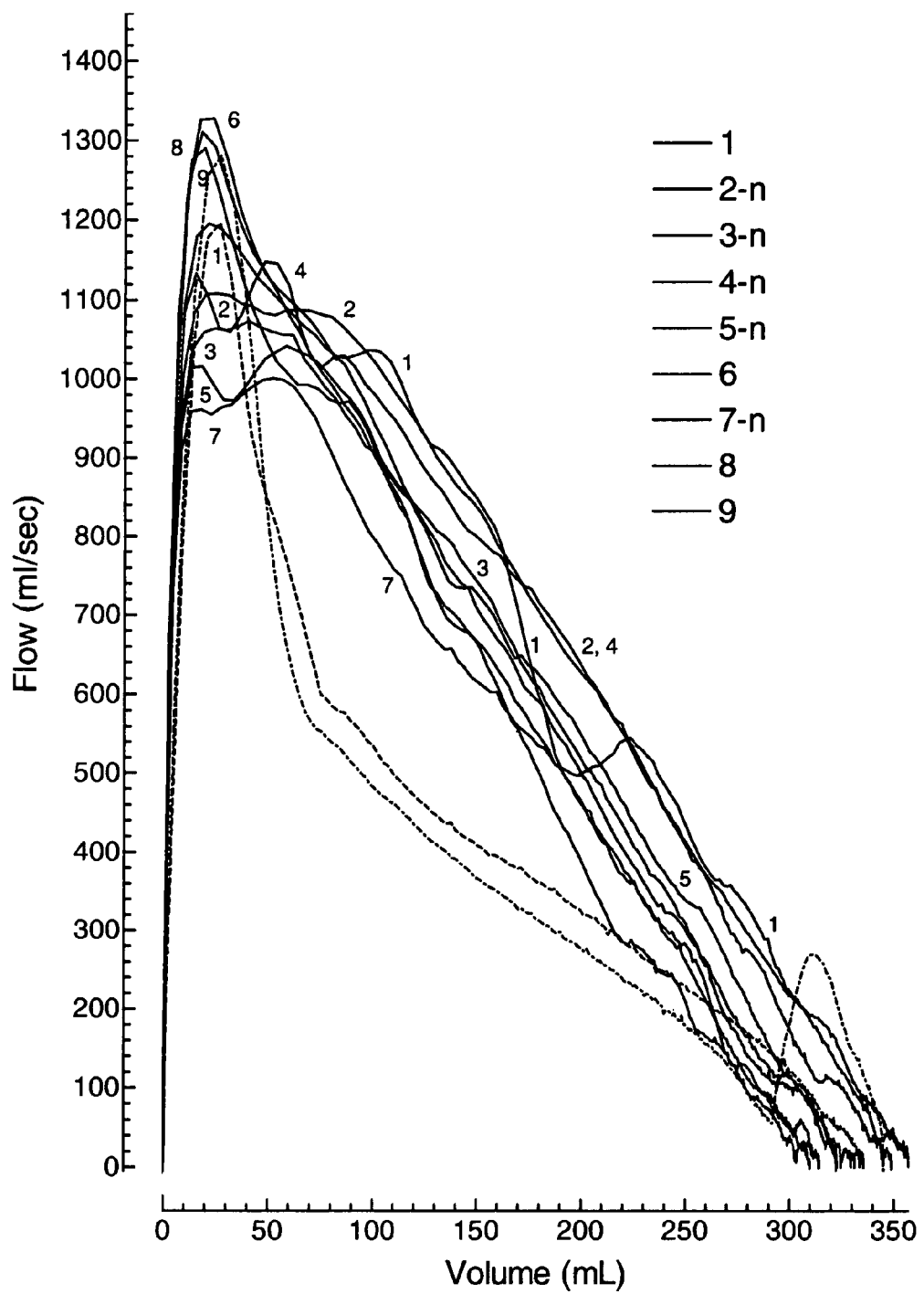
FIGS. 4A and 4B are flow-volume (F-V) curves of a 43 weeks old wheezer.
Figure 4B:
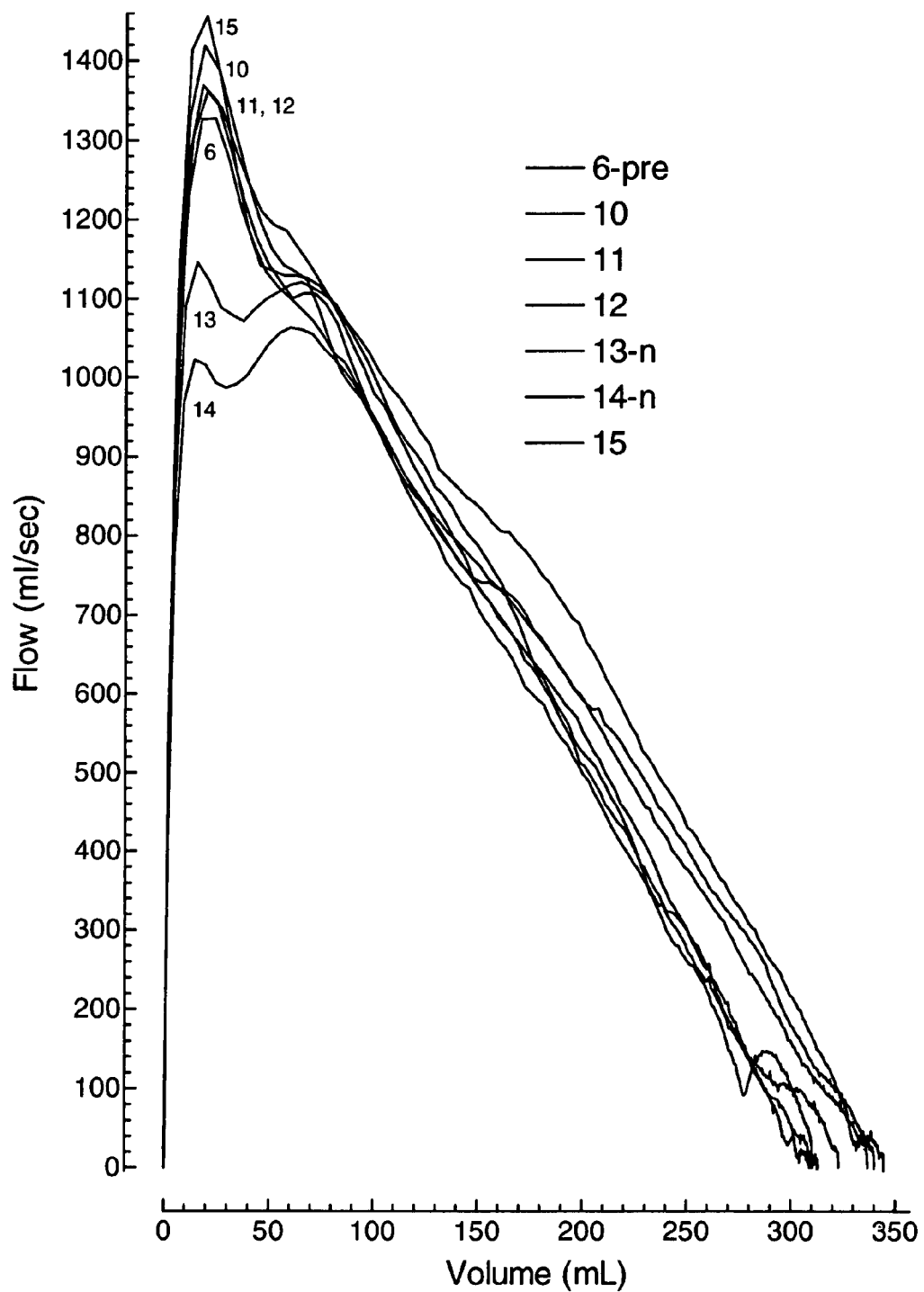

FIGS. 4A and 4B show flow-volume curves for a 43 weeks old wheezer. FIG. 4A presents flow-volume curves before giving albuterol. FEFV curve no. 1 exhibits the common initial undulations that disappear in subsequent curves and has PF of 1195 using Pj of 52.7 cm $H_2O$. However, progressive spontaneous mouth closure ensues in generating FEFV curves no. 2-5 via $FE_n$ with stifled peaks of maximum flow of 1109, 1073, 1148, 1042 ml/s, $V_{PEF}$/% FVC of 7.3, 12.5, 13.4 and 17.6%, with tEF of 1.505, 1.205, 1.445, 1.660 s using Pj of 54.5, 64.5, 53.2, and 57.8 cm $H_2O$ (not shown). Note that the higher Pj generated lower PF via $FE_n$ in curves no. 3 and 5. A re-opened mouth, generated via $FE_o$ curve no. 6 with a (higher) PF of 1328 ml/sec using Pj of 62.5 cm $H_2O$, $V_{PEF}$/%

FVC of 7.3%, tFE of 1.190 s. With the mouth spontaneously closing again, FEn generated curve no. 7 with stifled PF of 1001 ml/s, using Pj of 67.0 cm $H_2O$, $V_{PEF}$/% FVC of 5.5% and tFE of 1.410 s. The size 1.0 facemask and putty were removed and replaced after the mouth was again re-opened and curves no. 8 and 9 via $FE_o$ now have PF of 1311 and 1290 ml/s using Pj of 62.0 and 58.0 cm $H_2O$, $V_{PEF}$/% FVC of 5.5 and 5.7%, tFE of 1.515 and 1.510 s, respectively. Note also that the pEFV (IC) and the pFEFV (jSVC) have higher peaks than the $FE_n$-generated FEFV curves. The letter "n" in the FIGS. 4A and 4B indicate a nasal forced expiration.

The best FEFV curve (no. 6-pre) obtained before the administration of nebulized albuterol along with curves no. 10-15 generated starting ten minutes after are plotted in FIG. 4B on the same X-Y axes scale as in FIG. 4A. Note that FEFV curves no. 10-12 have PF of 1419, 1369 and 1361 ml/s, $V_{PEF}$/% FVC of 5.9, 5.7 and 6.3% and tFE of 1.295, 1250 and 1210 s, using Pj of 56.0, 62.7, and 66.0 cm $H_2O$, respectively. Progressive mouth closure partly spontaneously and partly by putty generated via $FE_n$ curves no. 13 and 14 which have stifled peaks of maximum flow of 1145 and 1063 ml/s, $V_{PEF}$/% FVC of 4.4% and 17.75, and tFE of 1.295 and 1.125 s, using Pj of 70.3 and 73.2 cm $H_2O$ respectively. Now, a size 2.0 facemask replaced the size 1.0 mask, and the $FE_o$-generated curve no. 15 has PF of 1455 ml/s, $V_{PEF}$/% FVC of 5.9% and tFE of 1.115 s using a Pj of 60.8 cm $H_2O$.

EXAMPLES

The method of the present invention was studied as detailed below:

The study inclusion criteria were the following: (1) gestational age of at least 37 weeks and birth weight at least 2.5 kg, (2) no more than an incidental second hand cigarette smoke exposure, and (3) no history other than transient respiratory problems during the neonatal period of less than 24 hr duration with a fractional inspiratory oxygen concentration of less than 0.3. Subject infants were excluded from testing if they were clinically unstable, had a significant upper airway obstruction, an acute respiratory illness three weeks prior to testing or a recent thoracic or abdominal surgical procedure. Depending on the infant's age, feeds were withheld and sleep deprivation was encouraged for about 2-4 hours before the patient was to be sedated. Parents were instructed to feed their baby breast milk or formula just prior to the fasting period. Depending on the age, subjects were sedated with 60-100 mg/kg chloral hydrate orally, rectally or both. A maximum dose of 1 g was not exceeded. Oral hydroxyzine, 0.25-0.5 mg/kg was used in addition for subjects weighing>10 kg or so for a synergistic sedative effect (18). After the full sedative dose was administered, a hungry crying infant was allowed to breastfeed for about three minutes or suck a few times on a bottle containing formula. Subjects were continuously monitored during the entire study with a pulse oximeter (Masimo Corporation, Irvine, Calif., USA).

Once asleep, the infant was placed supine on the testing table and a shoulder roll tilted the head back gently into a "sniffing" (neutral) position. During testing, the investigator placed one hand around and supported the mandible and his fingertips exerted a gentle pressure on the infant's cheeks between the upper and lower jaw in order to keep the mouth open and generate an oronasal not a nasal FE. His other hand held the valve assembly connected to the clear facemask embedded in firm putty maintaining an optimum gentle pressure on the mask against the infant's face to prevent air leaks. Both hands exerted a gentle coordinated anterior thrust on the lower jaw which facilitated the tidal breathing, lung inflations and FE especially during peak sedation. The valve assembly was disconnected from the facemask and a cannula carrying 2 L/min airflow was inserted into the mask port in between tests. Generally the dFRC was measured first, then jSVC-RV followed by the IC-sFRC or RVRTC. The technique of measuring the dFRC is well known in the prior art and is not discussed herein.

Figure 7:
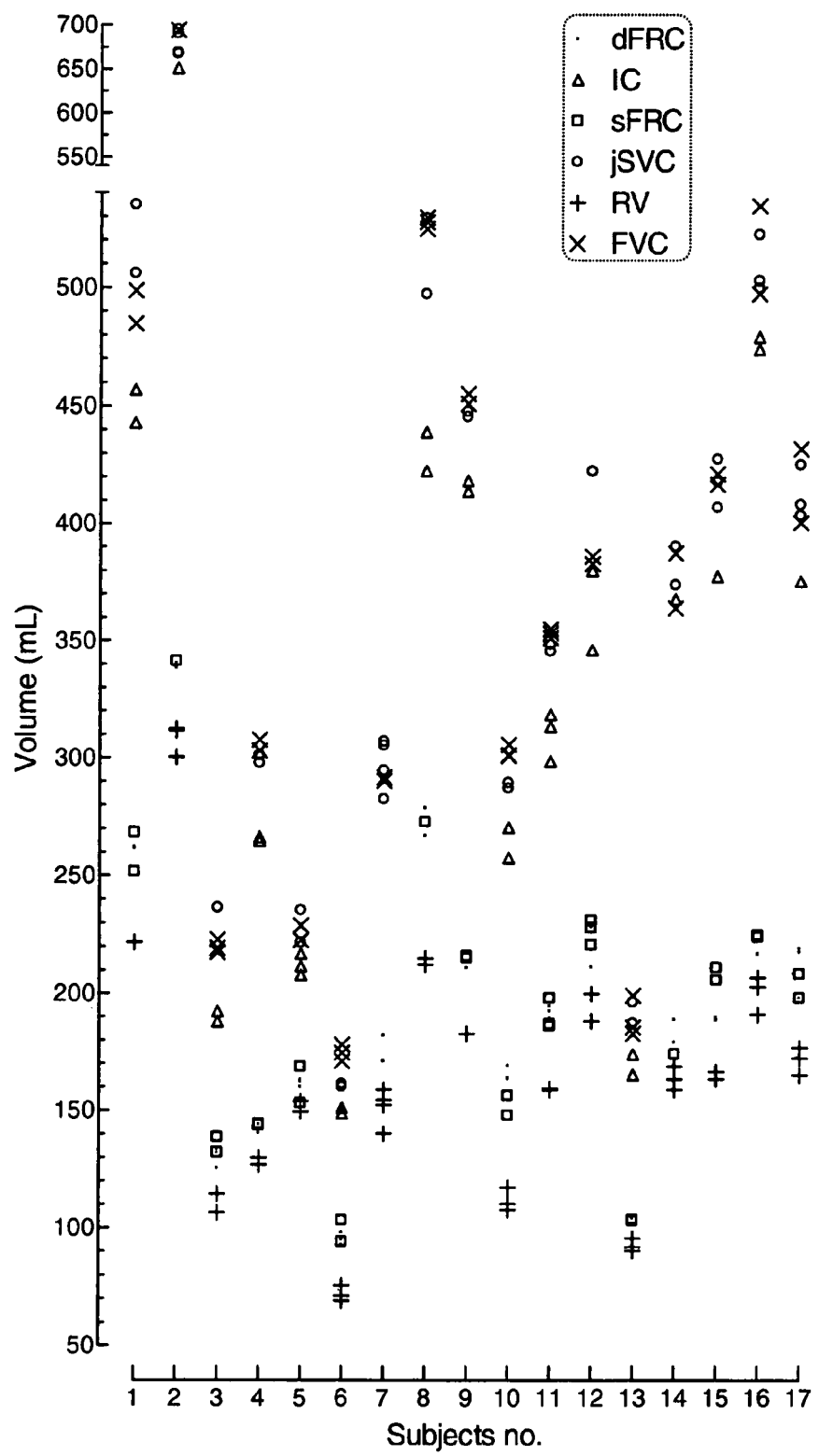
FIG. 7 is a dot plot showing individual dynamic (dFRC) and static (sFRC) functional residual capacity, inspiratory capacity (IC), slow vital capacity (jSVC), residual volume (RV) and forced vital capacity (FVC) measurements obtained from seventeen subjects.

FIG. 7 is a dot plot showing individual dynamic (dFRC) and static (sFRC) functional residual capacity, inspiratory capacity (IC), slow vital capacity (jSVC), residual volume (RV) and forced vital capacity (FVC) measurements obtained from seventeen subjects. RV and FRC were corrected for the dead space of the face mask and converted to BTPS. FRC was also corrected for the switching error above FRC. Note the high repeatability of measurements and the lack of overlap between RV and FRC measurements. Note also the overlap between FVC and jSVC and between the sFRC and dFRC measurements. Infant no. 2 had four and no. 6 two separate jSVC/RV measurements: 690.0/300.1, 694.5/312.3, 666.8/300.4 and 668/311.4; 161.1/75.5 and 160.0/71.2 ml, respectively. Infant no. 4 had two separate IC/sFRC measurements: 266.3/144.1 and 264.6/143.5 ml. Infants no. 5 and 11 had four separate dFRC measurements each: 159.7, 162.2, 162.9 and 150.1 ml; 189.2, 192.2, 184.2 and 194.3. Infant no. 2 had two and Infants no. 8, 10 and 11 had three separate FVC measurements each: 693.7 and 693.8; 524.4, 527.2 and 529.2 ml; 305.4, 300.7 and 301.1 ml; 354.9, 351.2 and 353.2 ml, respectively. Infant no. 9 had two separate measurements of the following: dFRC, 210.8 and 217.1, IC/sFRC, 413.5/215.7 and 418.2/215.1, jSVC/RV, 445.4/182.8 and 447.5/182.8 ml. Infant no. 12 had two separate jSVC measurements: 422.1 and 422.4 ml. Infant no. 13 and 15 had three separate RV measurements each: 91.8, 95.5 and 90.2; 163.2, 166.4 and 166.4 ml, respectively. FIG. 7 demonstrates that the reproducibility of the measurements in the seventeen subjects.

Figure 8:
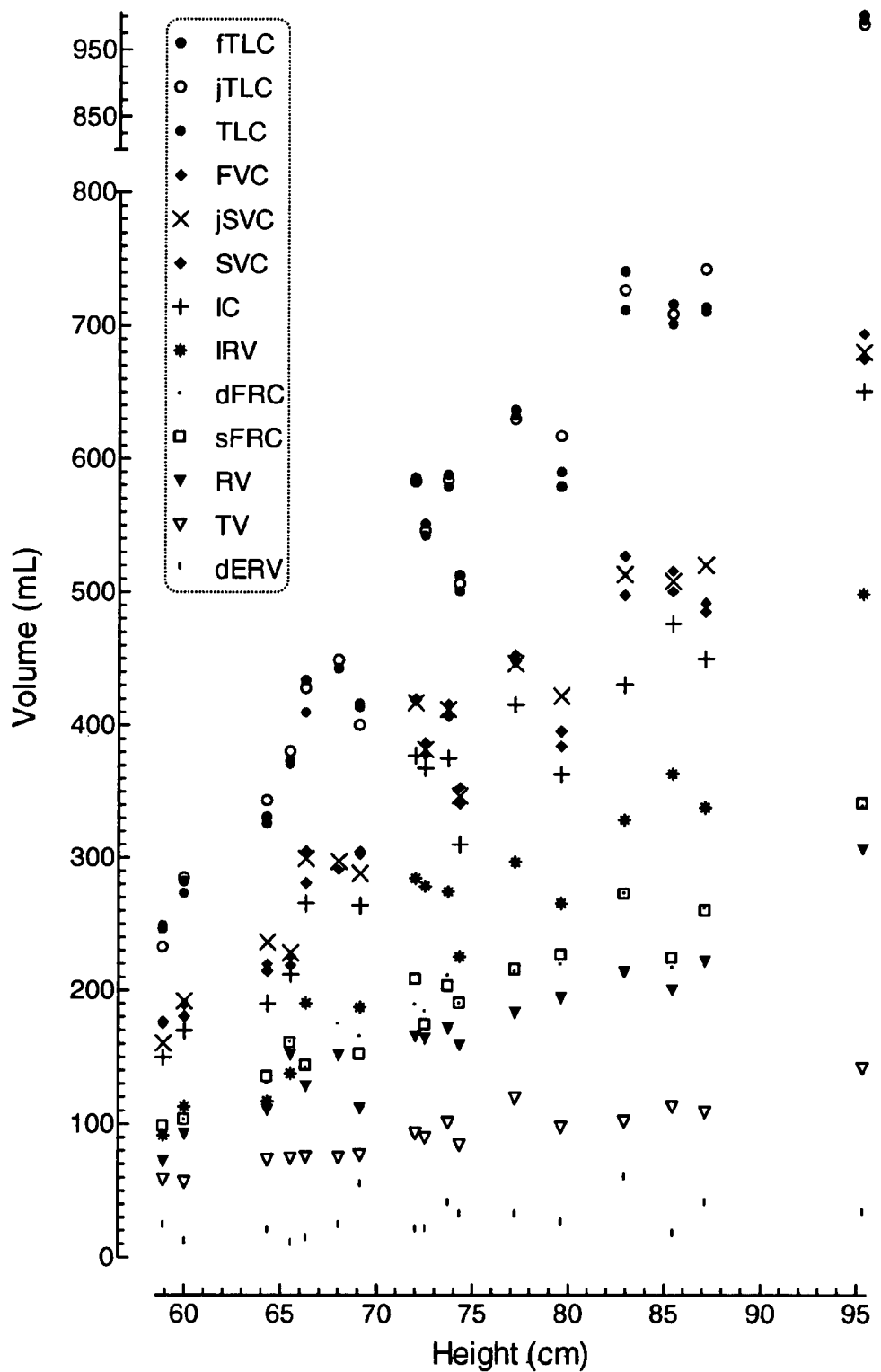
FIG. 8 is a scatter plot of individual height versus volumes and capacities.

FIG. 8 is a scatter plot of individual height versus volumes and capacities. FIG. 8 illustrates the concept of a comprehensive integrated protocol along with the significant result that measured as well as derived variables are height dependent.

FIGS. 9A-F are curves of passive (PEFV) (---), passive-forced (PFEFV) (_._._.) and forced (FEFV) (_) expiratory flow-volume (F-V) from a lung volume raised to an airway opening pressure of 30 cm $H_2O$ generating the inspiratory capacity (IC), slow vital capacity (jSVC) and forced vital capacity (FVC), respectively from infants no. 1, 2, 4, 8, 10 and 15. All were generated during a post-hyperventilation apnea (PHA) which continued for several seconds after end expiration (not shown). The F-V curves were aligned at total lung capacity (TLC). The abrupt increase in flow close to the end of the PFEFV curves is caused by the late jacket (j) activation which initiates a (partial) forced expiration to residual lung volume (RV) generating the jSVC which was within 5-10% of the FVC in each infant. Only the first and the best FEFV curves are shown from infant no. 2 to demonstrate the undulations in the former that disappeared in subsequent maneuvers presumably caused by an initial uneven jacket spread over the infant's chest and abdomen; however, the generated FVC was identical. Note that flow limitation was attained in the curves in each infant. Also, note the prominent peak of maximum flow which is higher in the FEFV than the PEFV and PFEFV curves. The F-V curves and measurements including the FVC from repeated raised volume rapid thoracoabdominal compression (RVRTC) maneuvers were smooth with high repeatability.

Measurement of the inspiratory capacity (IC) and static functional residual capacity (sFRC) was performed as follows: The infant was manually hyperventilated by intermittently occluding the expiratory limb of the Y-adapter and a post-hyperventilation apnea (PHA) was induced. As the lung volume was raised, Pao rose to a plateau set at 30 cm $H_2O$ by the pressure relief valve. Release of the expiratory thumb occlusion initiated the passive expiratory flow (F). The flow signal was integrated to produce volume (IC). There was an abrupt upward shift in Pao caused by the slide valve switching the infant into the constant bias flow of oxygen. Once the infant was switched into oxygen to begin measuring the sFRC, he/she no longer breathed through the pneumotachometer. Flow and Pao were both zero at the time of the switching indicating that the elastic equilibrium volume (EEV) of the respiratory system was attained. The onset of a negative deflection in the Pao trace signaled inspiration.

Measurement of the slow vital capacity (jSVC) and residual volume (RV) was performed as follows: The infant was manually hyperventilated by intermittently occluding the expiratory limb of the Y-adapter and a post-hyperventilation apnea (PHA) was induced. As the lung volume was raised, Pao rose to a plateau set at 30 cm $H_2O$ by the pressure relief valve. Close to the end of the passive expiration the jacket was activated, generating a positive small sharp peak (forced expiration) on the expiratory flow limb and a simultaneous tiny rise in Pao followed by a rapid return to zero. The flow signal was integrated to produce volume (V) which is jSVC. There was a very small abrupt upward shift in the Pao trace zero baseline caused by the switching of the infant into the bias flow of oxygen. Also a zero flow and a raised Pj plateau at the time of the switching occurred before the end of the Pj plateau, indicating chest compression (lungs were at RV). Once the infant was switched into $O_2$, he/she no longer breathed through the pneumotachometer. Pao remained steady indicating the lack of significant chest wall excursions and signaling the persistence of the PHA until the onset of a negative deflection (inspiration) in Pao.

Raised volume rapid thoracoabdominal compression was performed as follows: The infant was manually hyperventilated by intermittently occluding the expiratory limb of the Y-adapter and a post-hyperventilation apnea (PHA) was induced. As the lung volume was raised, Pao rose (iPao) to a preset (pPao) value, then the inflating airflow was (automatically) halted with the airway simultaneously occluded for a period of 0.20 s. The pPao dropped to a "true" actual (aPao) level and also a "true" zero flow and volume plateaued during this period. The jacket inflation began but the airway occlusion continued during which the rising Pj which was transmitted to the airway opening (jacket driving pressure) caused a second tiny rise in Pao. The occlusion was then terminated and forced expiration started and completed. The Pj plateau extended beyond end-expiration. No volume was (passively) exhaled prior to activating the jacket. Jacket deflation caused a simultaneous abrupt tiny increase in (passive inspiratory) flow which peaked due to the outward recoil of the chest wall to the elastic equilibrium volume of the respiratory system during the PHA.

Tables 1-6 are examples of CITP data for a particular test of an infant subject. The following abbreviations are used: n, number of tidal breaths; μ, mean (standard deviation); tPE, tFE, passive and forced expiratory time, respectively; tj, jacket compression time. "#" identifies each test. Volumes are in ml, pressures in cm $H_2O$, time in seconds. Sixteen 20-sec epochs of tidal breathing were recorded during testing with the number of tidal breaths per epoch ranging from 8-10. Similar maneuvers are grouped together with their actual sequence number shown. At least two measurements within 10% of each other were obtained. Five RVRTC maneuvers were performed. Measured FRC and RV were converted to BTPS. Note that repeated RVRTC did not affect subsequent sFRC or dFRC in #23, 25 and 27. Repeat nitrogen washouts did not affect measured volumes.

TABLE 1

Tidal Volume.

$\mu V_T$ = 84.5 (95% CI, 82.2 to 86.8)

TABLE 2

Dynamic FRC.

| #3 | dFRC = 189.2 |
|---|---|
| #5 | dFRC = 192.2 |
| #7 | dFRC = 184.2 |
| #23 | dFRC = 194.3 |
|  | μdFRC = 190.0 (4.4) |

Summarized in Table 3 following are the measurements of inspiratory capacity (IC). The expiratory flow signal was integrated to produce volume (IC). The infant was switched into the bias flow of pure oxygen after end-expiration during the post-hyperventilation apnea (PHA) to measure the sFRC by nitrogen washout.

TABLE 3

IC, raised volume, passive expiration (jacket unfastened).

| #14 IC = 298.5 | tPE = 2.120 s | sFRC = 186.6 | SUM = TLC = 485.1 |
|---|---|---|---|
| #25 IC = 313.2 | tPE = 1.940 s | sFRC = 197.8 | SUM = TLC = 511.0 |
| #27 IC = 318.3 | tPE = 2.270 s | sFRC = 186.0 | SUM = TLC = 504.3 |
| μIC = 310.0 (10.3) | μtPE = 2.110 (0.165) | μsFRC = 190.1 (6.7) | μTLC = 500.1 (13.4) |

The following Table 4 summarizes data for jSVC and RV. The expiratory flow signal was integrated to produce volume (jSVC). RV was estimated by measuring the volume of nitrogen expired after end forced expiratory switching of the inspired gas from room air to 100% oxygen while jacket inflation was maintained at the time of switching into oxygen during the PHA. jSVC and the derived jTLC assessed the potential limitation of jacket application on lung inflation to $V_{30}$.

TABLE 4 jSVC and RV, passive expiration with a (partial) forced expiration.

| #10 jSVC = 345.3 | RV = 158.7 | SUM = jTLC = 504.0 | Pj = 51.8 |
|---|---|---|---|
| #12 jSVC = 348.2 | RV = 159.2 | SUM = jTLC = 507.4 | Pj = 60.1 |
| μjSVC = 346.8 (2.1) | μRV = 159.0 (0.4) | μjTLC = 505.7 (2.4) | |

The following Table 5 summarizes FVC measurement. #20 below is considered the best curve according to consensus criteria of the American Thoracic Society and #16 is considered the next best curve. Note that in #20 aPao was lower but the FVC higher than in #17.

TABLE 5

FVC.

| #16 FVC = 354.9 | aPao = 29.7 | tFE = 1.615 | Pj = 37.7 | tj = 2 |
|---|---|---|---|---|
| #17 FVC = 351.2 | aPao = 29.7 | tFE = 1.605 | Pj = 45.7 | tj = 2 |
| #20 FVC = 353.2 | aPao = 29.4 | tFE = 1.530 | Pj = 50.6 | tj = 2.1 |
| μFVC = 353.1 (1.9) | μaPao = 29.6 (0.2) | μtFE = 1.583 (0.047) s | | |

Each of the following volumes or capacities was derived from two or more variables that each had been measured with a different maneuver or test. Individual derived variables are within 10% of comparable measured or derived ones. When comparing jTLC and fTLC with TLC, the values suggest no jacket limitation effect on chest inflation and no air trapping during the forced expiration, respectively; similarly, jRV and fRV versus RV.

TABLE 6

Derived volumes and capacities.

dERV OR sERV = dFRC OR sFRC − RV = {190.0 or 190.1}; mean ERV = 31.1
SVC = TLC − RV = 500.1 − 159.0 = 341.1
jIC = jTLC − FRC = 505.7 − 189.3 = 316.4
IRV = IC − VT = 310.0 − 84.5 = 225.5 OR
IRV = TLC − (ERV + VT + RV) = 500.1 − (31.1 + 84.5 + 159.0) = 225.5 OR
IRV = jTLC − (FRC + VT) = 505.7 − (190.1 + 84.5) = 231.1
fTLC = FVC + RV = 353.1 + 159.0 = 512.1
fIC = FVC − ERV = 353.1 − 31.1 = 322.0
fRV = TLC − FVC = 500.1 − 353.1 = 147.0
jRV = jTLC − FVC = 505.7 − 353.1 = 152.6

Figure 5A:
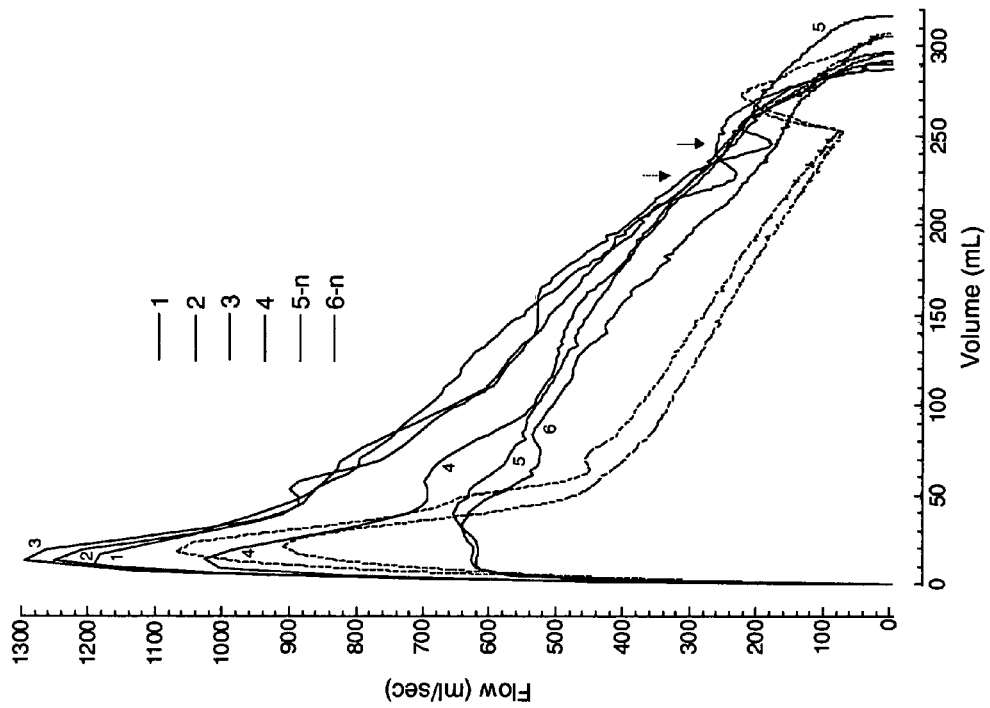
FIGS. 5A-D are sets of F-V curves of oronasal ($FE_O$) versus nasal forced expiration ($FE_n$) for four infant subjects.
Figure 5B:
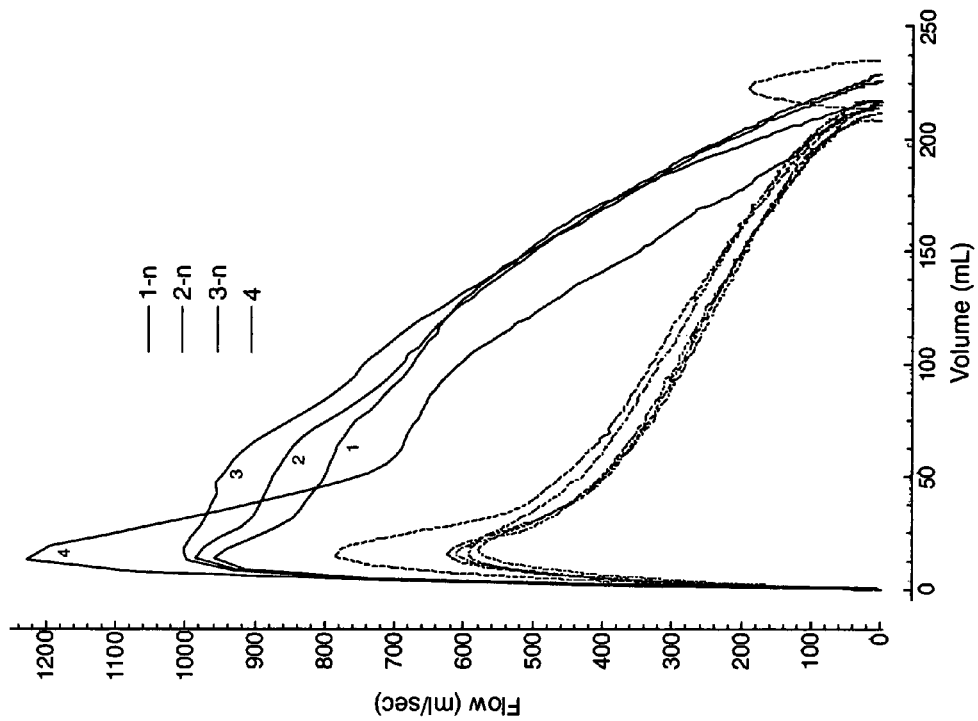

Examples of oronasal ($FE_o$) versus nasal forced expiration ($FE_n$) are given in FIGS. 5A-D. The letter "n" indicates a nasal forced expiration. Passive (PEFV) (_._._.), passive-forced (PFEFV) (----) and, using repeated raised volume rapid thoracoabdominal compressions (RVRTC) with increasing jacket pressures (Pj), the forced (FEFV) (-) expiratory flow-volume (F-V) curves from a lung volume raised to an airway opening pressure of 30 cm $H_2O$ generated the inspiratory capacity (IC), slow vital capacity (jSVC) and forced vital capacity (FVC), respectively from four infants as shown in FIGS. 5A-D, although the subject of FIG. 5B woke up before a PEFV curve could be performed. All were generated during a post-hyperventilation apnea (PHA) which continued for several seconds after end expiration (not shown). The F-V curves were aligned at total lung capacity (TLC). The abrupt increase in flow close to the end of the PFEFV curves is caused by the late jacket (j) activation which initiates a (partial) forced expiration to residual volume generating the jSVC. Numbers indicate the order of the FEFV curves generated. In infants whose curves are presented in FIGS. 5A and B a size no. 0 instead of no. 1 clear facemask which completely covered the nose and a closed mouth was applied, then three and two FEFV curves were generated, respectively, largely via a $FE_n$ to demonstrate the modulation of the forced expiratory flows (FEF). In the infant whose curves are shown in FIG. 5A, note that curves no. 1, 2 and 3 which were generated via a $FE_n$ using Pj (measured Pj signal plateau) of 46, 50 and 59 cm $H_2O$ (not shown), have stifled peaks of maximum flow (PF) 959, 984 and 1002.3 ml/sec, forced expiratory times (tFE) of 0.720, 0.965 and 0.840 s (not shown) and ratios of the expired volume at peak expiratory flow and FVC as percent ($V_{PEF}$/% FVC) of 6.1, 5.8 and 8.2%, respectively. Note also that (nasal) flow limitation was attained. A size no. 1 facemask which covered the nose and now an opened mouth was subsequently applied and curve no. 4 which was generated via an $FE_o$ using a Pj of 62 cm $H_2O$ has a prominent PF of 1228 ml/sec, tFE of 1.095 s and $V_{PEF}$/% FVC of 6.0% (the infant woke up after this maneuver). In the infant whose curves are shown in FIG. 5B, note that curves no. 1-4 which were generated via the $FE_o$ using Pj of 45, 43, 53 and 45.3 cm $H_2O$ have prominent PF of 1192, 1253, 1294 and 1027 ml/s, tFE of 0.885, 0.970, 1.055 and 0.880 s (not shown) and $V_{PEF}$/% FVC of 3.4, 4.4, 4.6 and 4.9%, whereas curves no. 5 and 6 generated via the $FE_n$ using Pj of 44.4 and 50 cm $H_2O$ have PF of 654 and 641 ml/s, tFE of 1.115 and 1.370 s and a $V_{PEF}$/% FVC ratio of 12.4 and 10.5%, respectively. Note also that curve no. 5 has supramaximal flows at very low lung volumes in spite of the low Pj used. Note a single flow transient at low lung volume in two $FE_o$-induced FEFV curves no. 1 and 3 reaching a nadir at volume points (arrows) of 245 and 228 ml respectively presumably caused by a venturi effect from the forced expiratory airflow transiently collapsing the airways.

Figure 5D:
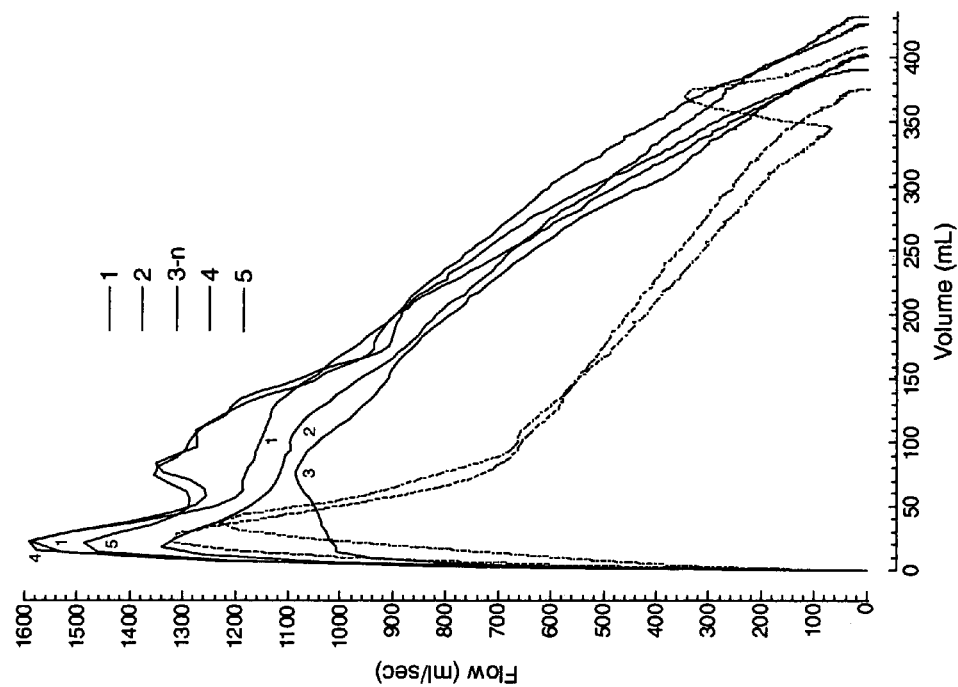
Figure 5C:
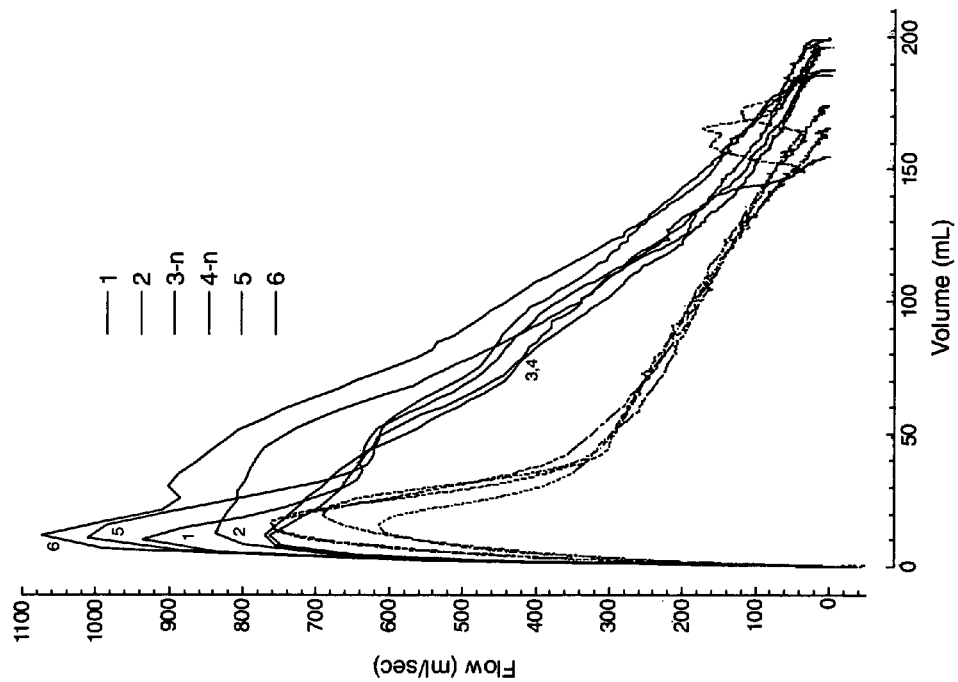

Spontaneous mouth closure occurred in the infants whose curves are presented in FIGS. 5C and D during the RVRTC which generated a $FE_n$ that resolved, that is a $FE_o$ was re-generated, when the facemask was removed and placed around the nose and a re-opened mouth. In the infant whose curves are presented in FIG. 5C, using Pj of 41, 45, 41 and 47 cm $H_2O$ note the prominent PF in curve no. 1 which gets lower in no. 2, and is stifled further in no. 3 and 4 measuring 936, 836, 762 and 771 ml/s with a tFE of 1.000, 0.840, 1.120 and 1.305 s (not shown) and $V_{PEF}$/% FVC of 5.4, 8.0, 6.2 and 6.3%, respectively, due to increasing nasal and decreasing oral airways contribution to the forced expiration, that is $FE_n$>$FE_o$. Note also that curve no. 2 has a small FVC (154.8 ml) that is ascribed to shunting of gas into the esophagus during the $FE_n$ and not an airleak since the FVC is higher in subsequent curves no. 3 and 4. The $FE_o$-generated curves no. 5 and 6 using a Pj of 41.7 and 49 cm $H_2O$ exhibit higher PF, 1010 and 1073 ml/s, have tFE of 1.420 and 1.125 s and $V_{PEF}$/% FVC of 5.4 and 5.9%, respectively. Note that flow limitation is attained by $FE_n$ and $FE_o$ but the FEF are modulated in the former. In the infant whose curves are shown in FIG. 5D using a Pj of 43, 48 and 58 cm $H_2O$, note that the (high) PF in curve no. 1 gets lower in no. 2 ($FE_n$>$FE_o$) and both delayed and lowest in no. 3 due to the $FE_n$, 1588, 1339 and 1084 ml/s, with tFE of 1.105, 1.280, and 0.950 s (not shown) and $V_{PEF}$/% FVC of 5.1, 4.4 and 19.7%, respectively. The re-opening of the mouth restored the $FE_o$ in curves no. 4 and 5 now having PF of 1594 and 1487 ml/s, tFE of 1.045 and 1.210 s and $V_{PEF}$/% FVC of 5.8 and 5.4% using Pj of 58 and 63 cm $H_2O$, respectively. Note in all infants except no. 5, that the PEFV and PFEFV curves exhibit higher PF than the FEFV curves generated via the $FE_n$ but not the $FE_o$ especially with a maximal nasal and minimal oral airways contribution to the forced expiration.

Tables 7-13 are examples of CITP data for particular tests of the infant subject of FIG. 5A. Similar maneuvers are grouped together with their actual sequence number shown. At least two measurements within 10% of each other were obtained and, except for RVRTC, no more than 2-3 tries were needed to attain this precision. Volume measurements are in milliliters (ml). Measured FRC and RV were converted to BTPS. Twenty-second or so epochs of tidal breathing were recorded in #1, 3, 6, and 9. Measurements marked "+" were recorded before switching the infant into the bias flow of pure $O_2$ to initiate the $N_2$ washout when measuring the dFRC in #6.

TABLE 7

Tidal Volume

3 $V_T$ = 63.3 (n = 6)
4 $V_T$ = 74.7 (n = 8)
+#5 $V_T$ = 64.5 (n = 5)
6 $V_T$ = 77.8 (n = 9)
7 $V_T$ = 64.7 (n = 5)
8 $V_T$ = 78.0 (n = 8)
11 $V_T$ = 71.1 (n = 9)

TABLE 7-continued

Tidal Volume

13 $V_T$ = 72.1 (n = 8)
19 $V_T$ = 80.7 (n = 8)
20 $V_T$ = 74.9 (n = 6)
*#21 $V_T$ = 80.0 (n = 8)
22 $V_T$ = 70.3 (n =)
23 $V_T$ = 80.4 (n = 7)
*#25 $V_T$ = 77.9 (n = 7)
26 $V_T$ = 71.2 (n =)
27 $V_T$ = 80.5 (n = 7)
29 $V_T$ = 80.5 (n = 7)

$\mu V_T$ = 74.3 (95% confidence interval, 71.2 to 77.4)

TABLE 8

Dynamic FRC

| | |
|---|---|
| #3 | dFRC = 159.7 |
| #20 | dFRC = 162.2 |
| #22 | dFRC = 162.9 |
| #26 | dFRC = 160.1 |
| | $\mu$dFRC = 161.2 |

Table 9 summarizes measurements of inspiratory capacity (IC). Those measurements marked "*" are raised volume, passive expiration from $V_{30}$ (jacket unfastened). The expiratory flow signal was integrated to produce volume (IC). The infant was switched into the bias flow of pure $O_2$ after end-expiration during the post-hyperventilation apnea (PHA) to measure the sFRC by $N_2$ washout.

TABLE 9

Inspiratory Capacity

| | | | |
|---|---|---|---|
| *#10 IC = 217.0 | tPE = 1.315 | sFRC = Excluded | SUM = TLC = — |
| *#24 IC = 211.5 | tPE = 1.390 | sFRC = 168.5 | SUM = TLC = 380 |
| #28 IC = 207.9 | tPE = 1.340 | sFRC = 152.9 | SUM = TLC = 360.8 |
| $\mu$IC = 212.1 | $\mu$tPE = 1.348 | $\mu$sFRC = 160.7 | $\mu$TLC = 370.4 |

The following table summarizes measurements of jSVC and RV. Passive expiration from $V_{30}$ was completed with an RTC-induced (partial) forced expiration. The expiratory flow signal was integrated to produce volume (jSVC). RV was estimated by measuring the volume of nitrogen expired after end forced expiratory switching of the inspired gas from room air to 100% oxygen while jacket inflation was maintained at the time of switching into oxygen during the PHA. jSVC and the derived jTLC assessed the potential limitation of jacket application on lung inflation to $V_{30}$.

TABLE 10 jSVC and RV

| | | | |
|---|---|---|---|
| **#12 jSVC = 221.3 | RV = 153.8 | SUM = jTLC = 375.1 | Pj = 48.1 |
| **#18 jSVC = 235.2 | RV = 149.4 | SUM = jTLC = 384.6 | Pj = 62 |
| $\mu$jSVC = 228.3 | $\mu$RV = 151.6 | $\mu$jTLC = 379.9 | |

The following Tables 11 and 12 summarize data associated with the oronasal and nasal FEFV curves. #17 is considered the best of the oronasal curves according to consensus criteria.

TABLE 11

Oronasal FEFV Curve

17 FVC = 216.3 mPao = 29.1; lowPao = 28.1 tFE$_0$ = 1.095 s Pj = 62.2
tj = 2 s PF = 1228.1 FEF$_{25-75}$ = 506.3 FEF$_{50-85}$ = 335.2 FEF$_{75}$ = 291.8
FEF$_{55}$ = 174.5
FEF$_{90}$ = 117.3
FEV$_{0.3}$ = 155.6 FEV$_{0.5}$ = 195.5 FEV$_{0.3}$/FVC = 0.72 FEV$_{0.4}$/FVC = 0.84
FEV$_{0.5}$/FVC = 0.90
V$_{PEF}$/% FVC = 13.0/%216.3 = 6.0% FVC + FEF$_{25-75}$ = 722.6 FVC + FEV$_{0.5}$ = 411.8

TABLE 12

Nasal FEFV Curve

14 FVC = 217.2 mPao = 29.9; lowPao = 29.1 tFE = 0.720 s
Pj = 46.4 tj = 2s
PF = 959.0 FEF$_{25-75}$ = 631.0 FEF$_{50-85}$ = 490.2 FEF$_{75}$ = 451.6 FEF$_{85}$ = 215.2
FEF$_{90}$ = 307.5
FEV$_{0.3}$ = 162.8 FEV$_{0.5}$ = 209.8 FEV$_{0.3}$/FVC = 0.75 FEV$_{0.4}$/FVC = 0.75
FEV$_{0.5}$/FVC = 0.97
V$_{PEF}$/% FVC = 13.3/%217.2 = 6.12% FVC + FEF$_{25-75}$ = 848.2
FVC + FEV$_{0.5}$ = 427
15 Highest FVC = 228.8 mPao = 29.7; lowPao = 28.7 tFE = 0.965 s
Pj = 49.7 tj = 2 s
PF = 984.0 FEF$_{25-75}$ = 609.4 FEF$_{50-85}$ = 442.7 FEF$_{75}$ = 392.8 FEF$_{85}$ = 262.6
FEF$_{90}$ = 181.7
FEV$_{03}$ = 167.1 FEV$_{0.5}$ = 215.8 FEV$_{0.3}$/FVC = 0.73 FEV$_{0.4}$/FVC = 0.73
FEV$_{0.5}$/FVC = 0.94
V$_{PEF}$/% FVC = 13.3/%228.8 = 5.8% FVC + FEF$_{25-75}$ = 838.2 FVC + FEV$_{0.5}$ = 444.6
16 FVC = 225.6 mPao = 29.6; lowPao = 29.1 tFE = 0.840 s Pj = 58.8 tj = 2s
PF = 1002.3 FEF$_{25-75}$ = 644.4 FEF$_{50-85}$ = 456.8 FEF$_{75}$ = 399.1 FEF$_{85}$ = 272.6
FEF$_{90}$ = 195.4
FEV$_{0.3}$ = 169.4 FEV$_{0.5}$ = 215.4 FEV$_{0.3}$/FVC 0.75 FEV$_{0.4}$/FVC = 0.89
FEV$_{0.5}$/FVC = 0.95
V$_{PEF}$/% FVC = 18.4/%225.6 = 8.2% FVC + FEF$_{25-75}$ = 870 FVC + FEV$_{0.5}$ = 441
$\mu$FVC = 223.9 tFE$_n$ = 0.842 Mean ALL FVCs = 222.0; mPao 29.6; lowPao = 28.8

Note that each volume or capacity in Table 13 below is derived from two or more variables that each had been measured with a different maneuver or test.

TABLE 13

Derived Volumes and Capacities dERV or sERV = Average dFRC and sFRC − RV = 161.0 − 151.6 = 9.4
ERV = FVC − IC = 222.0 − 212.1 = 9.9
SVC = TLC − RV = 370.4 − 151.6 = 218.8 (within 4.3% of jSVC OR
SVC = IC + ERV = 212.1 + 9.4 = 221.5
jIC = jTLC − dFRC or sFRC = 379.9 − 161.0 = 218.9
(within 3.2% of(IC) OR
jIC = jSVC − ERV = 228.3 − 9.4 = 218.9
IRV = IC − $V_T$ = 212.1 − 74.3 = 137.8 OR
IRV = TLC − (ERV + $V_T$ + RV) = 370.4 − (9.4 + 74.3 + 15 1.6) = 135.1 OR
IRV = jTLC − (dFRC or sFRC + $V_T$) = 379.9 − (161 + 74.3) = 144.6
(within 4.9 and 7% of the IRV above)
fTLC = FVC + RV = 222.0 + 151.6 = 373.0 (within 2% and 0.6% of j TLC and TLC respectively)
fIC = FVC − ERV = 222.0 − 9.4 = 212.6 (within 0.5% of XIC)
RV = TLC − FVC = 370.4 − 222.0 = 148.4 (within 2.8% of the measured RV) OR
RV = jTLC − FVC = 379.9 − 222.0 = 157.9
(within 3.8% of the measured RV)

When performing the IC-sFRC and the jSVC-RV maneuvers, confirmation that the lung volume is raised to a Pao of 30 cm $H_2O$ and, after end-expiration when the slide valve switches the infant into pure oxygen that the infant is in a PHA and the lungs are indeed at residual volume is achieved by analyzing the signals collected on the CCCS computer.

The RVRTC technique is primarily defined by lung inflation to a pPao. However, a true aPao reflective of the extent of lung inflation is crucial since lower Pao generates low FVC and can only be conclusively ascertained by occluding the airway for 0.20 s after terminating the inflating airflow and before activating the jacket inflation. This aPao is different from maintaining a fixed inflating (i) airflow of 15 or 12 L/min at $V_{30}$ (iPao) until the jacket inflation is triggered. Activating the jacket inflation without such occlusion could mask an actual Pao that is in fact lower than an observed "acceptable" iPao because the latter is just prevented from dropping by the rising jacket driving pressure induced at the airway opening by the RTC. Expectedly, attaining an exact 30.0 cm $H_2O$ aPao is unrealistic for the following reasons: (1) airways and lungs are distensible and do not conform to a single compartment model; (2) the slow opening of previously collapsed distal small airways (3) an iPao that is even equal to the pPao could be observed in real time on the computer monitor screen but might not have equilibrated with a "lower" pressure within the distal tracheobronchial tree especially if the fixed inflating airflow is high for a small infant or had masked a small circuit airleak which would manifest as a significant drop in aPao during the 0.02 s occlusion and a generated small FVC; (4) unsupported cheeks inflated while raising the lung volume generating an early smooth rise in Pao that has not equalized with the distal airway pressure and bulged during FE which could modulate peak flow; and (5) occasionally, especially during peak sedation a relatively high inflating airflow causes a transient upper airway collapse and obstruction by a venturi effect which would be relieved during the occlusion.

Halting the inflating airflow for 0.20 s during an airway occlusion before initiating $FE_o$ during automated RVRTC enhances the smoothness of FEFV curves which increases the reproducibility of the $FEF_{\%}$. The expiratory valve which opens after a 0.05 s delay after activating RTC, minimizes the volume of passively exhaled air prior to full jacket inflation as well as the jacket driving pressure, which is the number of cm $H_2O$ above the pPao of 30 cm $H_2O$, to about 0-3 cm $H_2O$ when the jacket becomes fully inflated which in turn minimizes the glottic closure flow transients artifacts and seems to facilitate peak flow and the achievement of flow limitation in the FEFV curves. An undesirably higher jacket driving pressure indicates a tight jacket placement and is abolished in subsequent RVRTC maneuvers by slightly loosening the jacket's firm vinyl outer layer. Placing the mini-balloon valve between the PNT and the Y-adapter and directing the bias airflow upwards toward the expiratory limb of the adapter away from the PNT minimizes the noise in the flow (F) signal baseline significantly such that flow calibration of the PNT with and without the bias airflow is virtually identical. The use of a single lung inflation-expiratory path during manually performed RVRTC with the PNT directly connected to the T-piece carrying the bias airflow in earlier reports generates FEFV curves that have significant flow transient artifacts likely caused by gas turbulence within the PNT between the bias airflow inflating the lungs and the exiting FEF especially if the thumb occlusion is not terminated in a timely fashion after activating RTC.

The solid state transducer, which exhibited an exceptional linearity when tested in vitro ($r^2=1.0$) and was placed close to the airway opening, terminated automated lung inflations at the exact pPao but the pressure-relief valve did not because pressure release at any adjusted pressure level was found to be dependent on its spatial position and the bias airflow rate used.

Compared to the impeller pump, the fine adjustments of the pneumatic circuit's airflow generate after 1-2 tries an automated last lung inflation that attained an aPao closest to 30 cm $H_2O$ without disturbing the sleeping infant. The constant bias airflow via the Y-adapter intended for the manual hyperventilation was adjusted differently according to the infant's size, tidal breathing pattern, depth of sedation and tolerance.

The sequence of various tests was often adapted to the individual infant. The RVRTC was performed when he/she was deeply sedated and dFRC when lightly sedated but has settled into quiet breathing. Chloral hydrate occasionally caused hypopnea with inefficient nitrogen washout so the RVRTC was performed instead. At peak sedation, another infant might have increased tendency for airway collapse and flow transients or gastric insufflation during the RVRTC, so the dFRC was then measured instead. Deeper sleep occurred sometimes later during testing and was ascribed to slow gastric emptying causing delayed drug absorption.

Gastric insufflation seemed virtually an inherent unwanted occurrence during raised volume maneuvers with some infants seemingly more susceptible than others especially during peak sedation. Contrary to studies which employed a fixed inflating flow rate to achieve an iPao and a "zero" inspiratory flow signal plateaus in real time, the presented automated RVRTC has only rarely caused significant epigastric distension, progressive decrease in FVC, affected other measurements or led to termination of ILFT. The risk of gastric insufflation was further minimized with these precautions: (1) adjusting the infant's head and neck using a shoulder roll instead of a head ring; (2) avoiding $FE_n$ which enhanced the diversion of the expiratory airflow to the esophagus by maintaining the mouth open; (3) using an optimum bias airflow relative to the infant's size; (4) limiting lung inflations during the hyperventilation to a Pao of 25 with the last two inflations closer to 30 cm $H_2O$ in order to ensure a robust PHA; (5) delaying or spacing out raised volume maneuvers during peak sedation to allow swallowed air to migrate to the distal intestines; (6) quickly aborting hyperventilation then re-adjusting the head and neck position before resuming inflations once a characteristic low pitch sound indicative of esophageal air entry was heard or palpated by the investigator holding the infant's chin, or a sudden change from a quick to a sluggish rise of the Pao signal during lung inflations was observed in real-time on the computer monitor screen which indicated the onset of an airleak or more likely gastric insufflation; (7) monitoring the epigastric region by palpation between measurements. Note that as described in Paragraphs [0096] and [0097], fifteen RVRTC measurements were performed without affecting the measured FVC in this infant. An adequately applied cricoid pressure (Sellick maneuver) aimed at preventing aerophagia would be painful or induce cough or vocal cords spasm since chloral hydrate is a hypnotic and not an analgesic drug and a gentle pressure would be inadequate. More importantly, it would interfere with the investigator's mandibular hold and adjustment of the head and neck. It was reported that ventilating infants via the oral route may or may not enhance the induction of gastric insufflation.

By using a calibrated heated PNT and the nitrogen washout in unison, the T-valve enabled single maneuvers with dual measurements to be performed with interdependence between measured gas volumes which enhanced the intrasubject analysis of the inter-relation between variables and interpretation of data by revealing physiological harmony or implausible differences between static and dynamic lung volumes. This added a quality assurance element to the CITP that would result in reliable physiological, technical as well as clinical interpretation of the variability in the data in an algorithmic fashion. For example, when measuring jSVC and RV within a single maneuver in a healthy infant: (1) a relatively large RV with a small jSVC along with an acceptable jTLC might indicate that a low Pj was used; (2) a significantly smaller jSVC than SVC and jTLC than TLC along with an acceptable RV might point to a tightly placed jacket around the infant which had limited lung inflation; the latter could result in a small FVC and fTLC also. Switching the infant prematurely into pure oxygen before end-passive expiration from $V_{30}$ would result in a small IC and a large sFRC despite an acceptable TLC. A small FVC could result from a very loosely applied jacket generating inadequate RTC or a tightly placed one that limited lung inflation, or gastric distension or a combination of these factors. Other examples that would alert the operator to a specific error in a measurement or the need to redo a maneuver: an IC>FVC, FVC>jSVC, RV> or =sFRC or dFRC, etc. A higher peak of maximum flow in the passive expiratory than the FEFV curves or a progressive decline in PF in the latter despite increasing Pj indicated a $FE_n$ and the need to re-open the mouth before resuming RVRTC. A higher peak flow was often noted in the jSVC than the IC F-V curves that was ascribed to the weight of jacket and attached hose rather than a tight jacket placement.

Respiratory diseases such as asthma, bronchopulmonary dysplasia and cystic fibrosis, all of which are associated with airways obstruction, air trapping, abnormal flow limitation and lung volume are present in early life. Rather than seeking the best test, the CITP measures multiple parameters that are relevant to the underlying pathophysiology, discriminates between health and disease and provides within-subject repeatability both within and between test occasions. It allows an unprecedented in-depth pathophysiological investigation of the nature, evolution of the early stages of not only these pulmonary diseases but also chest wall dysfunction and to quantify their severity as well as assess the efficacy of therapeutic interventions in early life and enhance our understanding of the acute or chronic effects of these respiratory disorders and how to prevent or minimize these effects.

In conclusion, the present invention is a conceptual, physiological and methodological approach for routine ILFT that emphasizes a CITP for measuring static and dynamic lung volumes and capacities at $V_{30}$. New and reproducible variables such as the IC, IRV, ERV, SVC and TLC, RV/TLC and FRC/TLC, tpE and tFE are described including comparable variables obtained with the jacket fastened around the infant such as the jSVC and jTLC. Maneuvers with dual measurements are valuable in infants because of the limited period of sleep-induced sedation. The ability to halt the inflating airflow and occlude the airway opening for 0.20 s prior to activating jacket inflation during automated RVRTC generates via $FE_o$ smooth FEFV curves in which flow limitation is achieved and enables the measurement of a "true" aPao that relates to the FVC and, if similarly automated, the passively exhaled volume from $V_{30}$ which tremendously facilitates future standardization of raised volume measurements. Moreover, the CITP incorporates powerful intrinsic quality control parameters by enabling the investigator to gain valuable algorithmic insights into intrasubject physiological or pathophysiological and crucial technical factors including the sequence of tests that might affect measured variables. This enables well-designed and executed longitudinal multicenter studies to undertake reliable inter-laboratory comparisons of data and track the lung function through the first three years of life and beyond.

The present invention has been described with reference to certain preferred and alternative embodiments that are intended to be exemplary only and not limiting to the full scope of the present invention as set forth in the appended claims. For example, the methods of the present invention have been described with reference to nitrogen washout techniques, although the present invention may be used with any known type of inert gas washout technique such as those techniques employing helium or sulfur hexafluoride.

What is claimed is:

1. A method for comprehensive integrated testing of lung function of an infant, comprising the steps of:
   hyperventilating the infant to induce post-hyperventilation apnea (PHA), and
   after end-passive expiration, measuring a static functional residual capacity (sFRC) by inert gas washout after said PHA following resumption of spontaneous respiration;
   wherein said step of measuring by inert gas washout comprises the steps of measuring a concentration of said inert gas with an inert gas analyzer and integrating electronically said concentration of said inert gas in a signal processing system.

2. The method of claim 1 further comprising the step of measuring a dynamic functional residual capacity (dFRC) in the infant.

3. The method of claim 1 wherein said inert gas washout technique is a nitrogen gas washout technique in which the infant's inspired air is switched to 100% oxygen during said PHA and said static functional residual capacity (sFRC) is measured by measuring a volume of nitrogen expired after said PHA following resumption of spontaneous respiration.

4. The method of claim 1, further comprising the steps of measuring an inspiratory capacity (IC) of the infant as a passively expired gas volume from an airway opening pressure plateau of 30 cm $H_2O$ through a pneumotachometer by integrating a flow signal to produce a volume and calculating a total lung capacity (TLC) as a sum of said sFRC and said IC.

5. The method of claim 4, wherein said steps of measuring said sFRC and said IC are accomplished in a single maneuver.

6. The method of claim 4, comprising the steps of measuring a forced vital capacity (FVC) and a residual volume (RV) in the infant and calculating an fTLC as a sum of said FVC and said RV.

7. The method of claim 6, further comprising the steps of calculating a slow vital capacity (SVC) as a difference between said TLC and said RV.

8. The method of claim 7, further comprising the step of comparing said SVC and said FVC to determine an existence of air trapping.

9. The method of claim 7 further comprising the steps of measuring a slow vital capacity obtained with a squeeze jacket placed on the infant (jSVC) by initiating rapid thoracoabdominal compression (RTC) during passive expiration from $V_{30}$ when said RV is measured.

10. The method of claim 9 further comprising the step of comparing said SVC and said jSVC to determine whether said squeeze jacket limits chest wall expansion of the infant.

11. The method of claim 9 further comprising the steps of calculating a jTLC as a sum of said jSVC and said RV and comparing said jTLC with said fTLC and said TLC.

12. The method of claim 11 further comprising the steps of calculating an fRV as a difference between said TLC and said FVC and a jRV as a difference between said jTLC and said FVC.

13. The method of claim 9, wherein said steps of measuring said jSVC and said RV are accomplished in a single maneuver.

14. The method of claim 13, wherein said jSVC is first measured with the infant breathing room air and said RV is measured by switching the infant from room air to 100% oxygen by a T-valve comprising a mini-balloon valve, a pneumatic slide valve and a pneumotachometer operatively disposed between said mini-balloon valve and said pneumatic slide valve.

15. The method of claim 14, wherein said T-valve further comprises a first bias air flow through said mini-balloon valve for manual inflation of the infant's lungs and a second bias air flow introduced between said mini-balloon valve and said pneumotachometer for automatic inflation of the infant's lungs.

16. The method of claim 14, wherein said T-valve further comprises a flow path having a constant flow bore equal to a constant flow bore of said pneumotachometer.

17. The method of claim 6 wherein said step of measuring said FVC occurs while the infant is maintained with an opened mouth and anterior jaw thrust.

18. The method of claim 6, including the steps of halting an inflating airflow and occluding the infant's airway opening for 0.20 s prior to activating jacket inflation during automated raised volume rapid thoracoabdominal compression (RVRTC) and measuring an airway ensemble average opening pressure (aPao).

19. The method of claim 6, wherein said steps of measuring said FVC and said RV are accomplished in a single automated maneuver.

20. The method of claim 19, wherein said FVC is first measured with the infant breathing room air and said RV is measured by switching the infant from room air to 100% oxygen by a T-valve comprising a mini-balloon valve, a pneumatic slide valve and a pneumotachometer operatively disposed between said mini-balloon valve and said pneumatic slide valve.

21. The method of claim 20, wherein said T-valve further comprises a first bias air flow through said mini-balloon valve for manual inflation of the infant's lungs and a second bias air flow introduced between said mini-balloon valve and said pneumotachometer for automatic inflation of the infant's lungs.

22. The method of claim 20, wherein said T-valve further comprises a flow path having a constant flow bore equal to a constant flow bore of said pneumotachometer.

23. The method of claim 4, wherein said IC is first measured with the infant breathing room air and the infant is switched from room air to 100% oxygen by a T-valve comprising a mini-balloon valve, a pneumatic slide valve and a pneumotachometer operatively disposed between said mini-balloon valve and said pneumatic slide valve.

24. The method of claim 23, wherein said T-valve further comprises a first bias air flow through said mini-balloon valve for manual inflation of the infant's lungs and a second bias air flow introduced between said mini-balloon valve and said pneumotachometer for automatic inflation of the infant's lungs.

25. The method of claim 23, wherein said T-valve further comprises a flow path having a constant flow bore equal to a constant flow bore of said pneumotachometer.

\* \* \* \* \*